US012774650B2

(12) United States Patent
Wang et al.

(10) Patent No.: US 12,774,650 B2
(45) **Date of Patent: *Oct. 27, 2026**

(54) OPTIMIZING A FIELD OPERATION THAT COMPRISES A GAS INJECTION

(71) Applicant: Chevron U.S.A. Inc., San Ramon, CA (US)

(72) Inventors: Wei Wang, Houston, TX (US); Wei Wei, Sugar Land, TX (US); Johannes Orlando Alvarez Ortiz, Houston, TX (US); Guo-Qing Tang, Mountain View, CA (US); Hao Sun, Houston, TX (US); Dengen Zhou, Sugar Land, TX (US); Kelly Marie Krezinski, Kingwood, TX (US); Chao Yan, Sugar Land, TX (US); Christopher Adam Griffith, Houston, TX (US); Jon Edward Burger, Houston, TX (US)

(73) Assignee: CHEVRON U.S.A. INC., San Ramon, CA (US)

( * ) Notice: Subject to any disclaimer, the term of this patent is extended or adjusted under 35 U.S.C. 154(b) by 413 days.

This patent is subject to a terminal disclaimer.

(21) Appl. No.: 18/385,775

(22) Filed: Oct. 31, 2023

(65) Prior Publication Data

US 2024/0141767 A1 May 2, 2024

Related U.S. Application Data

(60) Provisional application No. 63/420,798, filed on Oct. 31, 2022.

(51) Int. Cl.

*E21B 43/16* (2006.01)
*E21B 43/267* (2006.01)
*G01N 33/24* (2006.01)

(52) U.S. Cl.

CPC .......... *E21B 43/164* (2013.01); *E21B 43/267* (2013.01); *E21B 2200/20* (2020.05); *G01N 33/24* (2013.01)

(58) Field of Classification Search

CPC .... E21B 43/164; E21B 43/168; E21B 43/267; E21B 2200/20; G01N 33/24

See application file for complete search history.

(56) References Cited

U.S. PATENT DOCUMENTS

| | | | |
|---|---|---|---|
| 9,840,898 B2 | 12/2017 | Kasevich et al. | |
| 12,006,804 B2 * | 6/2024 | Abu-Khamsin | E21B 43/168 |

(Continued)

OTHER PUBLICATIONS

Mingyu Cai et al., CO2-Fluid-Rock Interactions and the Coupled Geomechanical Response during CCUS Processes in Unconventional Reservoirs, Published Feb. 26, 2021, 22 pages, Hindawai Geofluids, vol. 2021, Article ID 6671871, Wiley.

(Continued)

*Primary Examiner* — An H Do

(74) *Attorney, Agent, or Firm* — Smith & Woldesenbet Law Group, PLLC

(57) ABSTRACT

A method of improving a field operation that comprises a gas injection may include assessing a plurality of potential injection gases against a plurality of values of a plurality of parameters associated with a plurality of samples, where each of the plurality of potential injection gases comprises an acidic component, and where the plurality of parameters comprises fluid chemistry parameters and rock properties. The method may also include determining a proposed injection gas from among the plurality of potential injection gases for the field operation that comprises the gas injection to be performed using a first wellbore in fluidic communication with a first subterranean formation, a second wellbore in fluidic communication with the first subterranean formation, (Continued)

a third wellbore in fluidic communication with a second subterranean formation, or any combination thereof.

19 Claims, 13 Drawing Sheets

(56) References Cited

U.S. PATENT DOCUMENTS

| | | | | |
|---|---|---|---|---|
| 2015/0204170 | A1* | 7/2015 | Ayan | E21B 43/164 166/250.01 |
| 2021/0284899 | A1* | 9/2021 | Al-Nakhli | C09K 8/74 |

OTHER PUBLICATIONS

Mahendra K. Verma, Fundamentals of Carbon Dioxide-Enhanced Oil Recovery (CO2-EOR)—A Supporting Document of the Assessment Methodology For Hydrocarbon Recovery Using CO2-EOR Associated with Carbon Sequestration, 24 pages, Open-File Report 2015-1071, U.S. Geological Survey.

P. Ceragiolio et al., Alteration of Thermodynamic Equilibrium and Fluids-Rock Interactions during Acid Gas Injection into a Carbonate Sour Oil Reservoir, SPE 113920, Presented at 2008 SPE Europec/EAGE Annual Conference and Exhibition, Rome, Italy, Jun. 9-12, 2008, 13 pages.

Sanbo LV et al., Predicting the Effects of Acid Gas on Enhanced Oil Recovery in Hydrocarbon Gas Injection, SPE 108434-MS, Presented at the SPE Western Regional Meeting in Anchorage, Alaska, USA, May 23-26, 2016, 12 pages.

* cited by examiner

1097

1297
FIG. 12
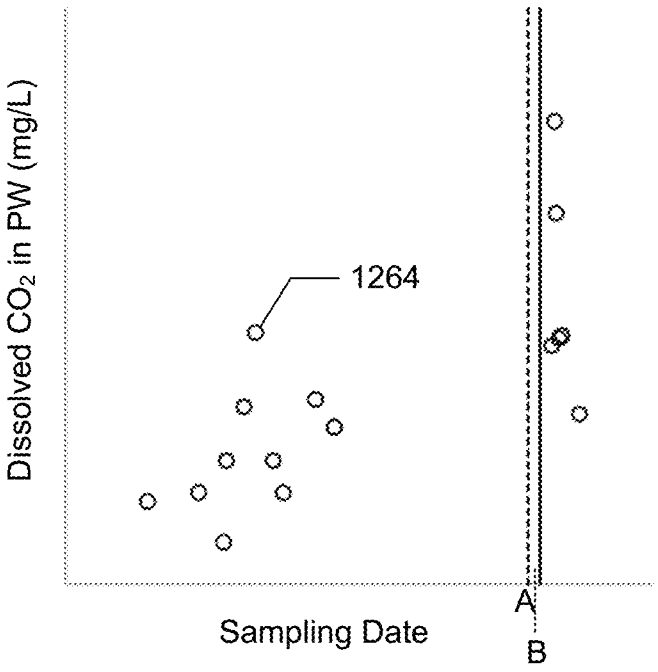
1397
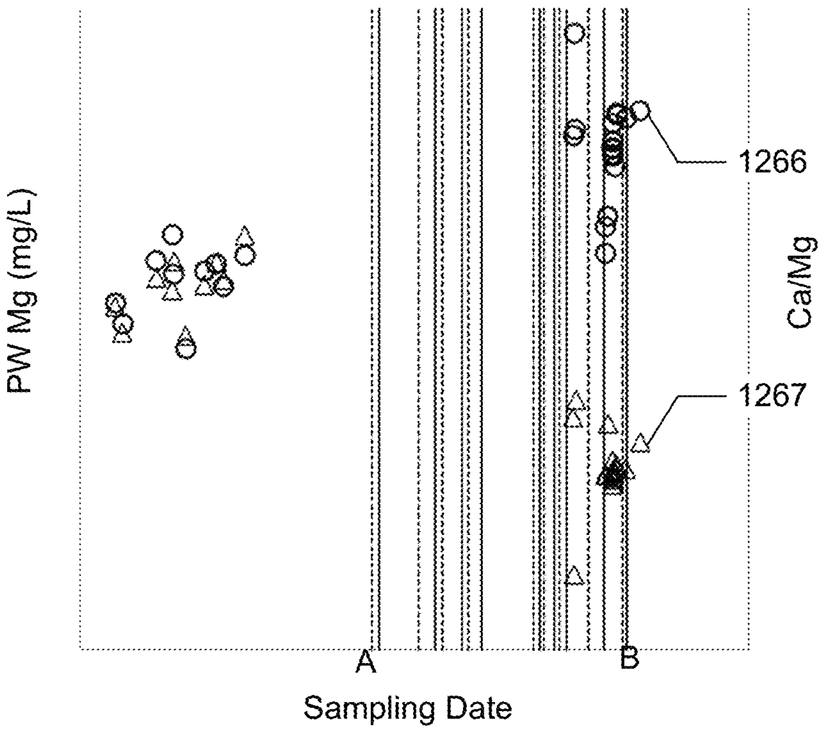
FIG. 13

1497

OPTIMIZING A FIELD OPERATION THAT COMPRISES A GAS INJECTION

CROSS-REFERENCE TO RELATED APPLICATIONS

This application claims priority under 35 U.S.C. § 119 to U.S. Provisional Patent Application Ser. No. 63/420,798, titled "Optimizing a Field Operation That Comprises a Gas Injection" and filed on Oct. 31, 2022, the entire contents of which are hereby incorporated herein by reference.

TECHNICAL FIELD

The present application is related to field operations and, more particularly, to optimizing a field operation that comprises a gas injection.

BACKGROUND

Gas injection is sometimes used for enhanced oil recovery (EOR) in field operations. The gas used for injection projects includes one or more components (e.g., $CH_4$, $C_2H_6$, $C_3H_8$, $C_4H_{10}$, $C_5H_{12}$, $C_6H_{14}$, $CO_2$, $H_2S$). The acidic gas compositions such as $CO_2$ and $H_2S$ may be present in produced gas and included in the injection gas. The acidic gas may have an impact on in situ water chemistry and water-rock/material interactions.

SUMMARY

In general, in one aspect, the disclosure relates to a method of improving a field operation that comprises a gas injection. The method may include assessing a plurality of potential injection gases against a plurality of values of a plurality of parameters associated with a plurality of samples, where each of the plurality of potential injection gases comprises an acidic component, and where the plurality of parameters comprises fluid chemistry parameters and rock properties. The method may also include determining, based on assessing the plurality of potential injection gases against the plurality of values of the plurality of parameters associated with the plurality of samples, a proposed injection gas from among the plurality of potential injection gases for the field operation that comprises the gas injection to be performed using a first wellbore in fluidic communication with a first subterranean formation, a second wellbore in fluidic communication with the first subterranean formation, a third wellbore in fluidic communication with a second subterranean formation, or any combination thereof.

In another aspect, the disclosure relates to a system for improving a field operation that comprises a gas injection. The system may include an analysis apparatus that is configured to assess a plurality of potential injection gases against a plurality of values of a plurality of parameters associated with a plurality of samples, where each of the plurality of potential injection gases comprises an acidic component, and where the plurality of parameters comprises fluid chemistry parameters and rock properties. The analysis apparatus of the system may also be configured to determine, based on assessing the plurality of potential injection gases against the plurality of values of the plurality of parameters associated with the plurality of samples, a proposed injection gas from among the plurality of potential injection gases for the field operation that comprises the gas injection to be performed using a first wellbore in fluidic communication with a first subterranean formation, a second wellbore in fluidic communication with the first subterranean formation, a third wellbore in fluidic communication with a second subterranean formation, or any combination thereof.

In yet another aspect, the disclosure relates to a computer-implemented method for improving a field operation that comprises a gas injection. The computer-implemented method may include receiving a plurality of values of a plurality of parameters associated with a plurality of samples, where the plurality of parameters comprises fluid chemistry parameters and rock properties. The computer-implemented method may include facilitate assessing a plurality of potential injection gases against the plurality of values of the plurality of parameters associated with a plurality of samples, where each of the plurality of potential injection gases comprises an acidic component. The computer-implemented method may include facilitate determining, based on facilitating assessment of the plurality of potential injection gases against the plurality of values of the plurality of parameters associated with the plurality of samples, a proposed injection gas from among the plurality of potential injection gases, where the proposed injection gas is used in the field operation comprising the gas injection to be performed using a first wellbore in fluidic communication with a first subterranean formation, a second wellbore in fluidic communication with the first subterranean formation, a third wellbore in fluidic communication with a second subterranean formation, or any combination thereof.

These and other aspects, objects, features, and embodiments will be apparent from the following description and the appended claims.

BRIEF DESCRIPTION OF THE DRAWINGS

The drawings illustrate only example embodiments and are therefore not to be considered limiting in scope, as the example embodiments may admit to other equally effective embodiments. The elements and features shown in the drawings are not necessarily to scale, emphasis instead being placed upon clearly illustrating the principles of the example embodiments. Additionally, certain dimensions or positions may be exaggerated to help visually convey such principles. In the drawings, reference numerals designate like or corresponding, but not necessarily identical, elements.

FIGS. 8 through 13 show graphs of a time lapse fluid chemistry study used to improve a field operation using a gas injection according to certain example embodiments.

DETAILED DESCRIPTION

Figure 1A:
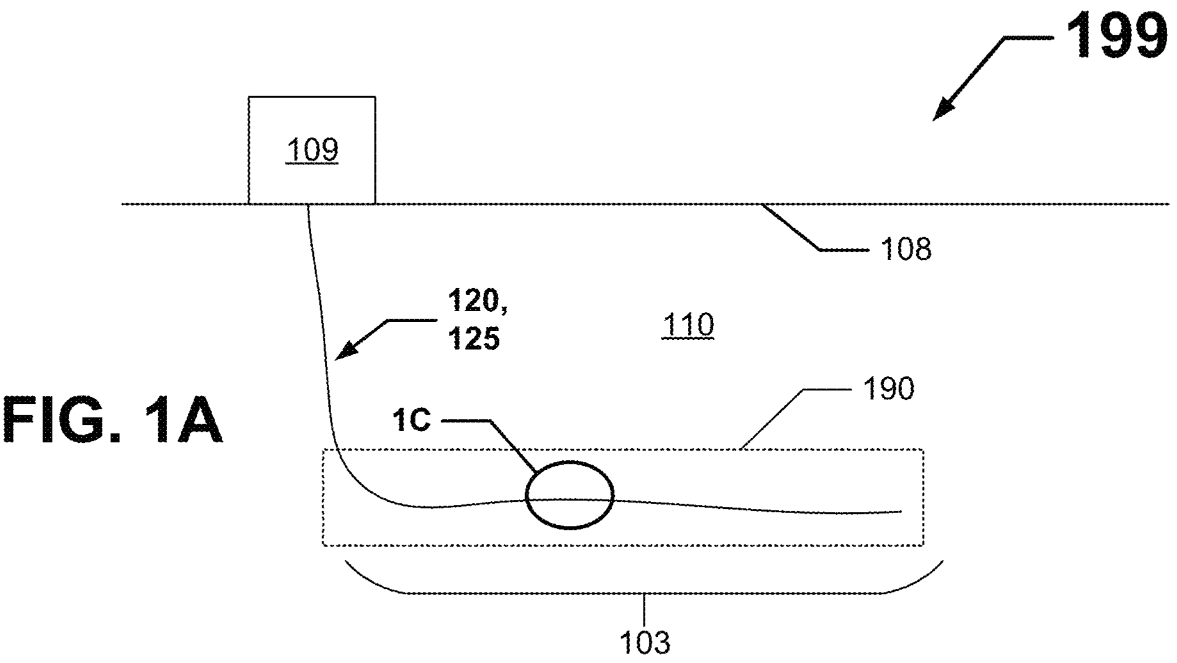
FIGS. 1A through 1D show field systems, and details thereof, with which example embodiments may be used.

The example embodiments discussed herein are directed to systems, apparatus, methods, and devices for optimizing (e.g., improving) a field operation comprising a gas injection. Gas injection is a method used for EOR. Gas diffusion-induced oil swelling (e.g., from fracture to matrix), solution gas drive (e.g., during pressure depletion), and high-pressure vaporization are examples of mechanisms for gas injection EOR for shale and tight rock reservoirs. Acidic gas (e.g., $CO_2$, $H_2S$) commonly exists as components in produced gas and injection gas. Also, acidic gas may partition into aqueous phase. In such a phase, the acidic gas may impact in-situ water chemistry and rock-water interaction, leading to potential change in rock porosity, wettability, and/or permeability, which may impact hydrocarbon release from rock. These chemical interactions between the injection gas with acidic components and the subterranean formation may lead to changes in important rock surface (e.g., frac face) characteristics such as porosity, permeability, and/or wettability.

Example embodiments are designed to factor these impacts of acidic gas (e.g., on water-rock interaction) to optimize (e.g., improve) a field operation comprising a gas injection. Example embodiments may also factor and minimize the effects that acidic gas in injection gas may have, including but not limited to, corrosion, scale accumulation, asphaltene deposition, and produced gas quality degradation due to acidic gas composition and/or the potential need to remove the acidic gas composition prior to sale.

In some cases, field operations that occur at the subsurface (e.g., in a fractured subterranean formation adjacent to a wellbore) may be improved, which may lead to additional subterranean resources being extracted from the subsurface and/or increasing the injection capacity and life of an injection wellbore. Examples of such additional subterranean resources may include, but are not limited to, hydrocarbons such as oil and natural gas. Use of example embodiments on production and injection wellbores may be designed to comply with certain standards and/or requirements. Example embodiments may be used for wellbores drilled in unconventional (e.g., shale and tight rock formations) and/or conventional subterranean formations. Example embodiments may be used for gas injection for enhanced hydrocarbon recovery and improved production performance from shale and tight rock reservoirs.

In some cases, optimizing (e.g., improving) a field operation comprising a gas injection may result in reducing deposition of scales and/or other solids, which may result in extracting a larger volume of subterranean resources from a subterranean formation for a longer period of time and/or extending the well life. As defined herein, reducing deposition of scales and/or other solids may involve any of a number of different actions. For example, reducing deposition of scales and/or other solids may include minimizing the accumulation or deposition of scales and/or other solids without completely eliminating the scales and/or other solids. As another example, reducing deposition of scales and/or other solids as defined herein may additionally or alternatively mean preventing the development of scale depositions and/or other solids. As yet another example, reducing deposition of scales and/or other solids as defined herein may additionally or alternatively mean completely eliminating scales and/or other solids that have previously developed. Optimizing (e.g., improving) a field operation comprising a gas injection may be applied in various scenarios, including but not limited to injection wells, processing facilities, and production wells.

Some benefits that may be realized using example embodiments may include, but are not limited to, simultaneously increasing EUR and lowering carbon via utilizing/trapping of acidic gases (e.g., $CO_2$, $H_2S$) to improve recovery and production performance, mineral trapping of $CO_2$, $CO_2$ utilization, and/or water chemistry surveillance for gas EOR. Example embodiments may be applied to different types of assets, including but not limited to shale and tight (S&T) reservoirs.

Example embodiments of optimizing (e.g., improving) a field operation comprising a gas injection may be at a subsurface (e.g., within and adjacent to a wellbore in a subterranean formation) for injection (e.g., salt water disposal (SWD), waterflooding) wells and production wells (e.g., wells undergoing a fracturing operation). Example embodiments of optimizing (e.g., improving) a gas injection technology may be applied for a field scenario under which gas and water streams are combined/pressurized to varying degrees and are injected for (i) EOR, (ii) water disposal, (iii) carbon capture, utilization, and storage, and/or (iv) other purposes. In certain field cases, the water may be treated to modify/enhance the water chemistry before the gas-water combination and/or for re-pressurization purposes. Multiphase pump injection may be applied for the combined gas-water system. Example embodiments of optimizing (e.g., improving) a field operation comprising a gas injection may additionally or alternatively be used in any of a number of other applications, including but not limited to waterflooding, EOR, and SWD. For instance, example embodiments may be used to reduce deposition of scales and/or other solids for improved performance in surface equipment. Such surface equipment may include, but is not limited to, heat exchangers and conduit or other pipes (e.g., a pipeline, a drainpipe) used to transport fluid (e.g., natural gas). As a specific example, example embodiments may be used to inject a gas (e.g., $CO_2$, gas streams containing $CO_2$) into water, with or without pressure, to make carbonate water. The resulting carbonate water may then be used for a fracturing operation and/or other field operations (e.g., production, SWD).

As defined herein, optimizing a field operation comprising a gas injection is based on identifying an injection gas (e.g., in terms of content, in terms of mixture, in terms of overall amount) that mixes with water (e.g., formation water, water used for a fracturing stage of a field operation, injection water used in a SWD well) and rock (e.g., formation rock) under field operational conditions. The injection gas may include one or more acidic compounds (e.g., $H_2S$, $CO_2$). Example embodiments identify the injection gas to be used, both in terms of the contents (e.g., acidic compounds, non-acidic compounds) of the injection gas and in terms of the concentration of each of the compounds of the injection gas. Optimizing may mean or include improving as defined herein. Optimizing may additionally or alternatively mean or include maximizing, increasing, and/or the like.

The injection gas established and used in example embodiments is designed to produce one or more of a number of results. Examples of such results may include, but are not limited to, increased porosity of the subterranean formation or porous media near fractures, increased permeability of the subterranean formation or porous media near fractures, changing of the content (e.g., chemistry (e.g., in situ pH), concentration) of the water (e.g., formation water, produced water, injection water) for different purposes (e.g., subsurface fracturing, salt water disposal via injection), reducing or eliminating the amount of a scale-generating component in the subterranean formation, and promoting rock-water interaction at the subsurface (e.g., mineral dissolution/transformation/precipitation).

As defined herein, water before gas injection may be of any type and/or from any source of water, including but not limited to produced water, without injecting gas, adding any chemicals, and/or making any other alterations to the water. Alternatively, water before gas injection may be of any type and/or from any source of water that has added thereto one or more chemicals and/or has otherwise been altered in some way that does not include introducing the injection gas discussed herein to the water. The water before gas injection may include one or more types of solid-generating components (e.g., bivalent cations, trivalent cations). In addition, the water before gas injection may include various amounts of total dissolved solids (TDSs) (e.g., greater than 1,000 mg/L, greater than 30,000 mg/L). In some cases, there may be no water injection (e.g., hydraulic fracturing, water alternating gas injection (WAG), combined and pressurized gas water injection (e.g., for enhanced oil recovery such as waterflooding and gas EOR, water disposal, hydraulic fracturing, mineral trapping of $CO_2$)) prior to gas injection operations. In such cases, the injected gas may still interact with in situ water in the near wellbore region once injected downhole, such as with shale formations and/or other tight formations.

A field operation may be defined as a series of steps and/or procedures performed on a subterranean formation. Examples of a field operation may be or include, but are not limited to, drilling a wellbore, inserting casing, pumping cement, fracturing, gas injection, water injection, mineral trapping, and production of subterranean resources. There may be multiple field operations performed from a common location (e.g., a platform, topsides of a floating structure). For example, field operations (e.g., the same field operation, different field operations) may be performed simultaneously on multiple wellbores that originate from a common pad. A field operation may have a single stage or multiple stages. For example, a fracturing operation may be performed multiple times on a single wellbore.

It is understood that when combinations, subsets, groups, etc. of elements are disclosed (e.g., combinations of components in a composition, or combinations of steps in a method), that while specific reference of each of the various individual and collective combinations and permutations of these elements may not be explicitly disclosed, each is specifically contemplated and described herein. By way of example, if an item is described herein as including a component of type A, a component of type B, a component of type C, or any combination thereof, it is understood that this phrase describes all of the various individual and collective combinations and permutations of these components. For example, in some embodiments, the item described by this phrase could include only a component of type A. In some embodiments, the item described by this phrase could include only a component of type B. In some embodiments, the item described by this phrase could include only a component of type C. In some embodiments, the item described by this phrase could include a component of type A and a component of type B. In some embodiments, the item described by this phrase could include a component of type A and a component of type C. In some embodiments, the item described by this phrase could include a component of type B and a component of type C. In some embodiments, the item described by this phrase could include a component of type A, a component of type B, and a component of type C. In some embodiments, the item described by this phrase could include two or more components of type A (e.g., A1 and A2). In some embodiments, the item described by this phrase could include two or more components of type B (e.g., B1 and B2). In some embodiments, the item described by this phrase could include two or more components of type C (e.g., C1 and C2). In some embodiments, the item described by this phrase could include two or more of a first component (e.g., two or more components of type A (A1 and A2)), optionally one or more of a second component (e.g., optionally one or more components of type B), and optionally one or more of a third component (e.g., optionally one or more components of type C). In some embodiments, the item described by this phrase could include two or more of a first component (e.g., two or more components of type B (B1 and B2)), optionally one or more of a second component (e.g., optionally one or more components of type A), and optionally one or more of a third component (e.g., optionally one or more components of type C). In some embodiments, the item described by this phrase could include two or more of a first component (e.g., two or more components of type C (C1 and C2)), optionally one or more of a second component (e.g., optionally one or more components of type A), and optionally one or more of a third component (e.g., optionally one or more components of type B).

The use of the terms "about", "approximately", and similar terms applies to all numeric values, whether or not explicitly indicated. These terms generally refer to a range of numbers that one of ordinary skill in the art would consider as a reasonable amount of deviation to the recited numeric values (i.e., having the equivalent function or result). For example, this term may be construed as including a deviation of ±10 percent of the given numeric value provided such a deviation does not alter the end function or result of the value. Therefore, a value of about 1% may be construed to be a range from 0.9% to 1.1%. Furthermore, a range may be construed to include the start and the end of the range. For example, a range of 10% to 20% (i.e., range of 10%-20%) includes 10% and also includes 20%, and includes percentages in between 10% and 20%, unless explicitly stated otherwise herein. Similarly, a range of between 10% and 20% (i.e., range between 10%-20%) includes 10% and also includes 20%, and includes percentages in between 10% and 20%, unless explicitly stated otherwise herein.

A "subterranean formation" refers to practically any volume under a surface. For example, it may be practically any volume under a terrestrial surface (e.g., a land surface), practically any volume under a seafloor, etc. Each subsurface volume of interest may have a variety of characteristics, such as petrophysical rock properties, reservoir fluid properties, reservoir conditions, hydrocarbon properties, or any combination thereof. For example, each subsurface volume of interest may be associated with one or more of: temperature, porosity, salinity, permeability, water composition, mineralogy, hydrocarbon type, hydrocarbon quantity, reservoir location, pressure, etc. Those of ordinary skill in the art will appreciate that the characteristics are many, including, but not limited to: shale gas, shale oil, tight gas, tight oil, tight carbonate, carbonate, vuggy carbonate, unconventional (e.g., a permeability of less than 25 millidarcy (mD) such as a permeability of from 0.000001 mD to 25 mD)), diatomite, geothermal, mineral, etc. The terms "formation", "subsurface formation", "hydrocarbon-b earing formation", "reservoir", "subsurface reservoir", "subsurface area of interest", "subsurface region of interest", "subsurface volume of interest", and the like may be used synonymously. The term "subterranean formation" is not limited to any description or configuration described herein.

A "well" or a "wellbore" refers to a single hole, usually cylindrical, that is drilled into a subsurface volume of interest. A well or a wellbore may be drilled in one or more directions. For example, a well or a wellbore may include a vertical well, a horizontal well, a deviated well, and/or other type of well. A well or a wellbore may be drilled in the subterranean formation for exploration and/or recovery of resources. A plurality of wells (e.g., tens to hundreds of wells) or a plurality of wellbores are often used in a field depending on the desired outcome.

A well or a wellbore may be drilled into a subsurface volume of interest using practically any drilling technique and equipment known in the art, such as geosteering, directional drilling, etc. Drilling the well may include using a tool, such as a drilling tool that includes a drill bit and a drill string. Drilling fluid, such as drilling mud, may be used while drilling in order to cool the drill tool and remove cuttings. Other tools may also be used while drilling or after drilling, such as measurement-while-drilling (MWD) tools, seismic-while-drilling (SWD) tools, wireline tools, logging-while-drilling (LWD) tools, or other downhole tools. After drilling to a predetermined depth, the drill string and the drill bit may be removed, and then the casing, the tubing, and/or other equipment may be installed according to the design of the well. The equipment to be used in drilling the well may be dependent on the design of the well, the subterranean formation, the hydrocarbons, and/or other factors.

A well may include a plurality of components, such as, but not limited to, a casing, a liner, a tubing string, a sensor, a packer, a screen, a gravel pack, artificial lift equipment (e.g., an electric submersible pump (ESP)), and/or other components. If a well is drilled offshore, the well may include one or more of the previous components plus other offshore components, such as a riser. A well may also include equipment to control fluid flow into the well, control fluid flow out of the well, or any combination thereof. For example, a well may include a wellhead, a choke, a valve, and/or other control devices. These control devices may be located on the surface, in the subsurface (e.g., downhole in the well), or any combination thereof. In some embodiments, the same control devices may be used to control fluid flow into and out of the well. In some embodiments, different control devices may be used to control fluid flow into and out of a well. In some embodiments, the rate of flow of fluids through the well may depend on the fluid handling capacities of the surface facility that is in fluidic communication with the well. The equipment to be used in controlling fluid flow into and out of a well may be dependent on the well, the subsurface region, the surface facility, and/or other factors. Moreover, sand control equipment and/or sand monitoring equipment may also be installed (e.g., downhole and/or on the surface). A well may also include any completion hardware that is not discussed separately. The term "well" may be used synonymously with the terms "borehole," "wellbore," or "well bore." The term "well" is not limited to any description or configuration described herein.

If a component of a figure is described but not expressly shown or labeled in that figure, the label used for a corresponding component in another figure may be inferred to that component. Conversely, if a component in a figure is labeled but is not described, the description for such component may be substantially the same as the description for the corresponding component in another figure. The numbering scheme for the various components in the figures herein is such that each component is a three-digit number or a four-digit number, and corresponding components in other figures have the identical last two digits. For any figure shown and described herein, one or more of the components may be omitted, added, repeated, and/or substituted. Accordingly, embodiments shown in a particular figure should not be considered limited to the specific arrangements of components shown in such figure.

Further, a statement that a particular embodiment (e.g., as shown in a figure herein) does not have a particular feature or component does not mean, unless expressly stated, that such embodiment is not capable of having such feature or component. For example, for purposes of present or future claims herein, a feature or component that is described as not being included in an example embodiment shown in one or more particular drawings is capable of being included in one or more claims that correspond to such one or more particular drawings herein.

Example embodiments of optimizing a field operation comprising a gas injection will be described more fully hereinafter with reference to the accompanying drawings, in which example embodiments of optimizing a field operation comprising a gas injection are shown. Optimizing a field operation comprising a gas injection may, however, be embodied in many different forms and should not be construed as limited to the example embodiments set forth herein. Rather, these example embodiments are provided so that this disclosure will be thorough and complete, and will fully convey the scope of optimizing a field operation comprising a gas injection to those of ordinary skill in the art. Like, but not necessarily the same, elements (also sometimes called components) in the various figures are denoted by like reference numerals for consistency.

Terms such as "first", "second", "primary," "secondary," "above", "below", "inner", "outer", "distal", "proximal", "end", "top", "bottom", "upper", "lower", "side", "left", "right", "front", "rear", and "within", when present, are used merely to distinguish one component (or part of a component or state of a component) from another. This list of terms is not exclusive. Such terms are not meant to denote a preference or a particular orientation, and they are not meant to limit embodiments of optimizing a field operation comprising a gas injection. In the following detailed description of the example embodiments, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Figure 1B:
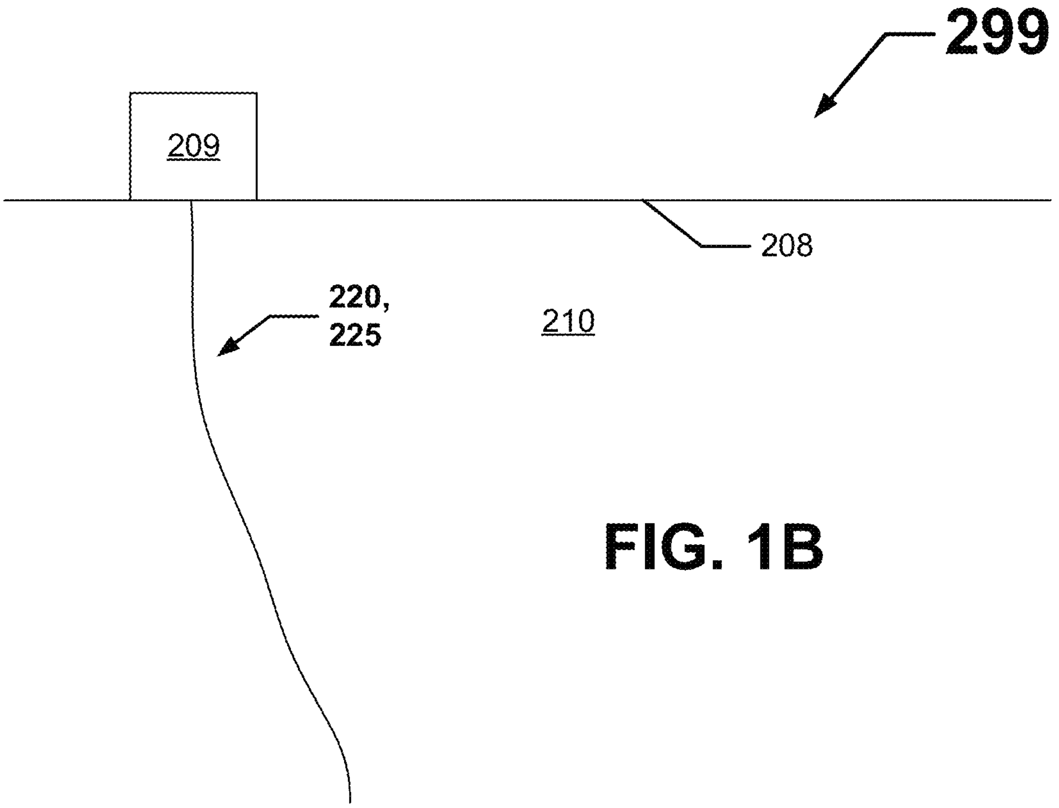
Figure 1C:
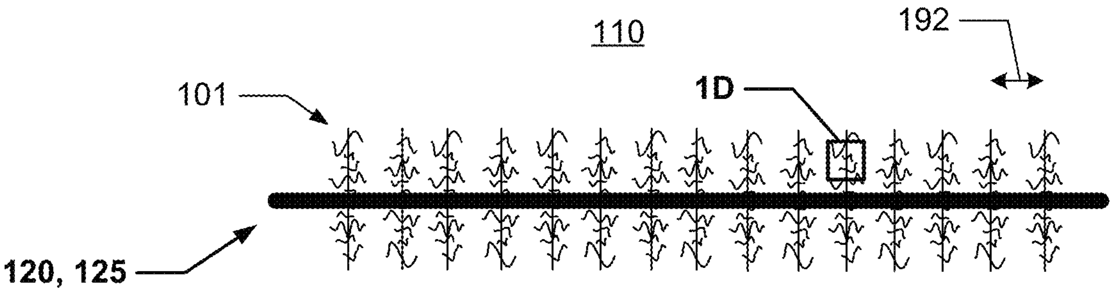
Figure 1D:
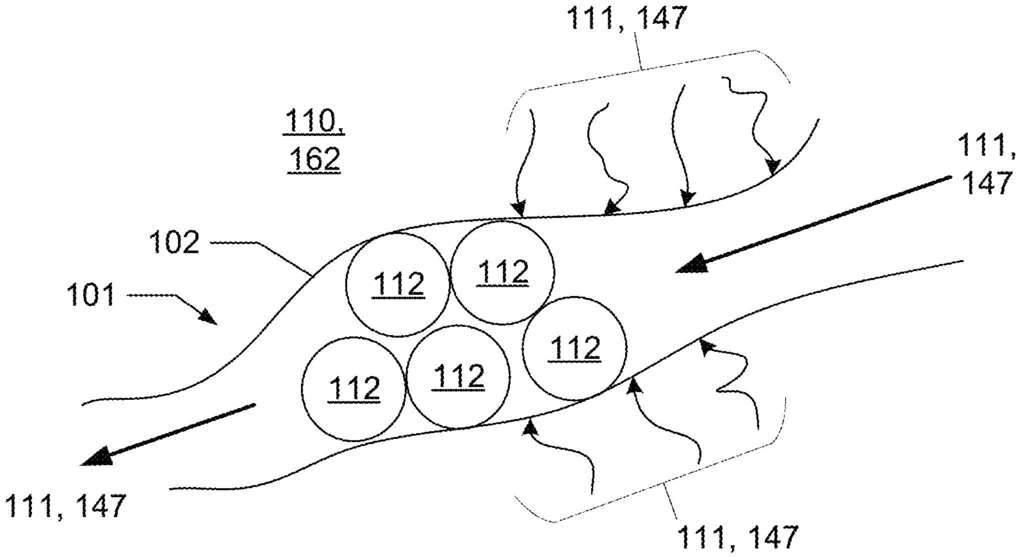

FIGS. 1A through 1D show a field system 199, including details thereof, with which example embodiments may be used. Specifically, FIG. 1A shows a schematic diagram of a land-based field system 199 in which a wellbore 120 has been drilled in a subterranean formation 110 and in which optimizing a field operation comprising a gas injection may be performed using example embodiments. FIG. 1B shows a schematic diagram of another land-based field system 299 in which a wellbore 220 has been drilled in a subterranean formation 210 and in which optimizing a field operation comprising a gas injection may be performed using example embodiments. FIG. 1C shows a detail of a substantially horizontal section 103 of the wellbore 120 of FIG. 1A. FIG. 1D shows a detail of an induced fracture 101 of FIG. 1C. The field system 199 of FIG. 1A includes a producing wellbore 120 disposed in a subterranean formation 110 using field equipment 109 (e.g., a derrick, a tool pusher, a clamp, a tong, drill pipe, casing pipe, a drill bit, a wireline tool, a fluid pumping system) located above a surface 108 and within the wellbore 120. Example embodiments may also be used in other types of wells (e.g., injection wells) that have vertical sections (as in FIGS. 1A and 1B) and/or horizontal sections (as in FIG. 1A).

With respect to the system 199 of FIG. 1A, once the wellbore 120 is drilled, a casing string 125 is inserted into the wellbore 120 to stabilize the wellbore 120 and allow for the extraction of subterranean resources (e.g., natural gas, oil, produced water) from the subterranean formation 110. Field equipment 109, located at the surface 108, is used to drill, encase, fracture, produce, and/or perform any other part of a field operation with respect to the wellbore 120. The wellbore 120 of FIG. 1A starts out as substantially vertical, and then has a substantially horizontal section 103. This configuration of the wellbore 120 is common for exploration and production of subterranean resources, such as oil and natural gas.

Similarly, with respect to the system 299 of FIG. 1B, once the wellbore 220 is drilled, a casing string 225 is inserted into the wellbore 220 to stabilize the wellbore 220 from the subterranean formation 210. Field equipment 209, located at the surface 208, is used to drill, encase, fracture, produce, and/or perform any other part of a field operation with respect to the wellbore 220. The wellbore 220 of FIG. 1B is substantially vertical. This configuration of the wellbore 220 is common for injection wells.

Referring back to FIG. 1A, the surface 108 may be ground level for an onshore application and the sea floor (or other similar floor under a body of water) for an offshore application. A body of water may include, but it not limited to, sea water, brackish water, flowback or produced water, wastewater (e.g., reclaimed or recycled), brine (e.g., reservoir or synthetic brine), fresh water (e.g., fresh water comprises <1,000 ppm TDS), any other type of water, or any combination thereof. For offshore applications, at least some of the field equipment may be located on a platform that sits above the water level. The point where the wellbore 120 begins at the surface 108 may be called the wellhead. While not shown in FIGS. 1A and 1B, there may be multiple wellbores 120, 220, each with its own wellhead but that is located close to the other wellheads, drilled into the subterranean formation 110, 210 and having substantially vertical sections and/or horizontal sections 103 that are close to each other. In such a case, the multiple wellbores 120, 220 may be drilled at the same pad or at different pads.

During the process of drilling the wellbore 120 of FIG. 1A, (and similarly for the wellbore 220 of FIG. 2), samples in the form of cuttings, produced water 147, and/or other subterranean resources 111 (e.g., relatively small amounts of oil or natural gas) are extracted from downhole to the surface 108, where some of the field equipment 109 separates out at least some of the cuttings and recirculates the produced water 147 back downhole. When the drilling process is complete, other operations, such as fracturing operations, may be performed. Throughout each of these various operations, fluids are circulated from the surface 108 by the field equipment 109, and samples are collected and tested for any of a number of parameters.

While the subterranean formation 110 has naturally-occurring fractures and some fractures that are induced when drilling the wellbore 120, these fractures may need to be enlarged and elongated, and additional fractures need to be induced, in order to extract additional subterranean resources 111 (e.g., oil, natural gas) from the subsurface. Fracturing operations accomplish these goals. The fractures 101 are shown to be located in the horizontal section 103 of the wellbore 120 in FIG. 1C. The fractures 101, whether induced and/or naturally occurring, may additionally or alternatively be located in other sections (e.g., a substantially vertical section, a transition area between a vertical section and a horizontal section) of a wellbore (e.g., wellbore 120, wellbore 220).

The subterranean formation 110 may include one or more of a number of formation types, including but not limited to shale, limestone, sandstone, clay, sand, and salt. In certain embodiments, a subterranean formation 110 may include one or more reservoirs in which one or more resources (e.g., oil, natural gas, water, steam) may be located. One or more of a number of field operations (e.g., fracturing, coring, tripping, drilling, setting casing, extracting downhole resources) may be performed to reach an objective of a user with respect to the subterranean formation 110.

The wellbore 120 may have one or more of a number of segments or hole sections, where each segment or hole section may have one or more of a number of dimensions. Examples of such dimensions may include, but are not limited to, a size (e.g., diameter) of the wellbore 120, a curvature of the wellbore 120, a total vertical depth of the wellbore 120, a measured depth of the wellbore 120, and a horizontal displacement of the wellbore 120. There may be multiple overlapping casing strings of various sizes (e.g., length, outer diameter) contained within and between these segments or hole sections to ensure the integrity of the wellbore construction. In this case, one or more of the segments of the subterranean wellbore 120 is the substantially horizontal section 103.

Figure 2:
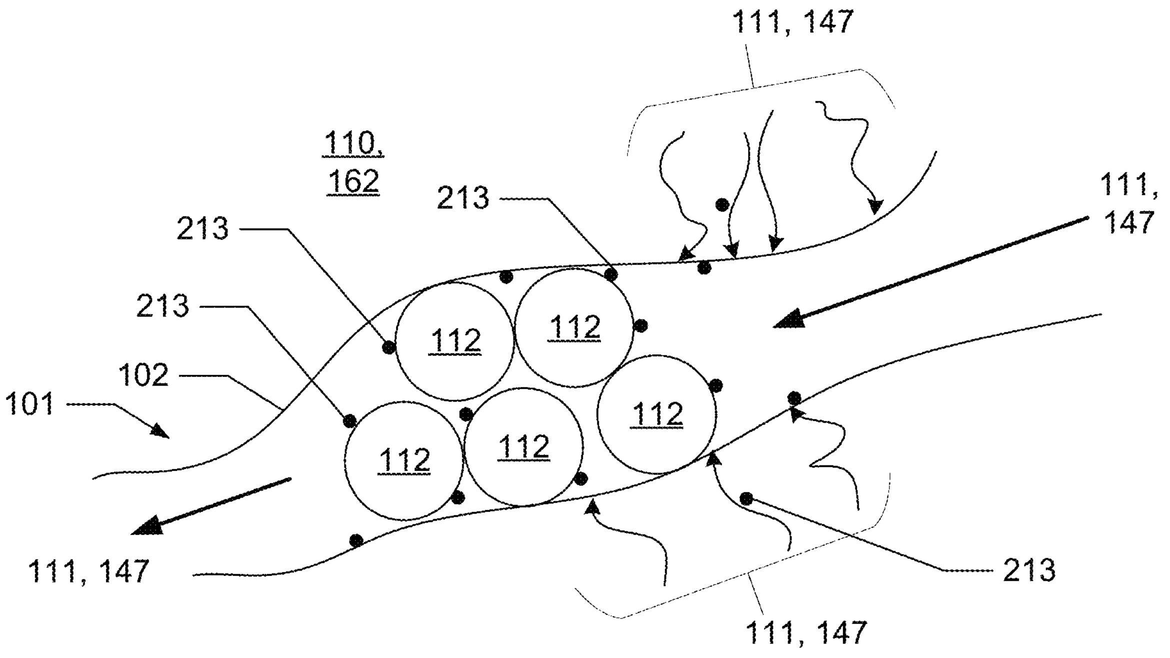
FIG. 2 shows the detail of FIG. 1D at a subsequent point in time according to certain example embodiments.

As discussed above, inserted into and disposed within the wellbore 120 of FIGS. 1A and 1C are a number of casing pipes that are coupled to each other end-to-end to form the casing string 125. Similarly, inserted into and disposed within the wellbore 220 of FIG. 2 are a number of casing pipes that are coupled to each other end-to-end to form the casing string 225. In this case, each end of a casing pipe has mating threads (a type of coupling feature) disposed thereon, allowing a casing pipe to be directly or indirectly mechanically coupled to another casing pipe in an end-to-end configuration. The casing pipes of the casing string 125 and the casing string 225 may be indirectly mechanically coupled to each other using a coupling device, such as a coupling sleeve.

Each casing pipe of the casing string 125 and each casing pipe of the casing string 225 may have a length and a width (e.g., outer diameter). The length of a casing pipe may vary. For example, a common length of a casing pipe is approximately 40 feet. The length of a casing pipe may be longer (e.g., 60 feet) or shorter (e.g., 10 feet) than 40 feet. The width of a casing pipe may also vary and may depend on the cross-sectional shape of the casing pipe. For example, when the shape of the casing pipe is cylindrical, the width may refer to an outer diameter, an inner diameter, or some other form of measurement of the casing pipe. Examples of a width in terms of an outer diameter may include, but are not limited to, 4½ inches, 7 inches, 7⅝ inches, 8⅝ inches, 10¾ inches, 13⅜ inches, and 14 inches.

The size (e.g., width, length) of the casing string 125 and the casing string 225 may be based on the information (e.g., diameter of the borehole drilled) gathered using field equipment with respect to the subterranean wellbore 120 and the subterranean wellbore 220. The walls of the casing string 125 and the casing string 225 have an inner surface that forms a cavity that traverses the length of the casing string 125 and the casing string 225. Each casing pipe may be made of one or more of a number of suitable materials, including but not limited to steel. Cement is poured into the wellbore 120 and the wellbore 220 through the cavity and then forced upward between the outer surface of the casing string 125 and the wall of the subterranean wellbore 120 and between the outer surface of the casing string 225 and the wall of the subterranean wellbore 220. In some cases, a liner may additionally be used with, or alternatively be used in place of, some or all of the casing pipes.

Referring to FIGS. 1A, 1C, and 1D, but with principals that may equally apply to FIG. 1B, once the cement dries and cures, a number of fractures 101 are induced in the subterranean formation 110. The fractures 101 may be induced in any of a number of ways known in the industry, including but not limited to hydraulic fracturing, fracturing using electrodes, and/or other methods of inducing fractures. The hydraulic fracturing process involves the injection of large quantities of fluids containing water, chemical additives, and proppant 112 into the subterranean formation 110 from the wellbore 120 to create fracture networks. An example of fracturing using electrodes may be found in U.S. Pat. No. 9,840,898 issued on Dec. 12, 2017, to Kasevich et al., the entirety of which is herein incorporated by reference. A subterranean formation 110 naturally has fractures 101, but these naturally occurring fractures 101 have inconsistent characteristics (e.g., length, spacing) and so in some cases may not be relied upon for extracting subterranean resources without having additional fractures 101, such as what is shown in FIG. 1C, induced in the subterranean formation 110.

Operations that induce fractures 101 in the subterranean formation 110 use any of a number of fluids that include proppant 112 (e.g., sand, ceramic pellets). When proppant 112 is used, some of the fractures 101 (also sometimes called principal fractures, primary fractures, or propped fractures) receive proppant 112, while a remainder of the fractures 101 (also sometimes called secondary fractures or unpropped fractures) do not have any proppant 112 in them.

As shown in FIG. 1D, the proppant 112 is designed to become lodged inside at least some of the induced fractures 101 to keep those fractures 101 open after the fracturing operation is complete. The size of the proppant 112 may be an important design consideration. Sizes (e.g., 40/70 mesh, 50/140 mesh) of the proppant 112 may vary. While the shape of the proppant 112 is shown as being uniformly spherical, and the size is substantially identical among the proppant 112, the actual sizes and shapes of the proppant 112 may vary. If the proppant 112 is too small, the proppant 112 will not be effective at keeping the fractures 101 open enough to effectively allow produced water 147 and/or other subterranean resources 111 to flow through the fractures 101 from the rock matrices 162 in the subterranean formation 110 to the wellbore 120. If the proppant 112 is too large, the proppant 112 may plug up the fractures 101, blocking the flow of the produced water 147 and/or other subterranean resources 111 through the fractures 101.

The use of proppant 112 in certain types of subterranean formations 110, such as shale, is important. Shale formations typically have permeabilities on the order of microdarcys (μD) to nanodarcys (nD). When fractures 101 are induced in such formations with low permeabilities, it is important to sustain the fractures 101 and their permeability and conductivity for an extended period of time in order to extract more of the subterranean resource 111. During fracturing procedures for a production well and during injection for an injection well, the flow of the subterranean resources 111 and the produced water 147 shown in FIG. 1D is replaced in the opposite direction with fracturing fluid and injection fluid, respectively.

The various induced fractures 101 that originate at the wellbore 120 and extend outward into the rock matrices 162 in the subterranean formation 110 in this case have consistent penetration lengths perpendicular to the wellbore 120 and have consistent coverage along at least a portion of the lateral length (substantially horizontal section) of the wellbore 120. For example, induced fractures 101 may be 50 meters high and 200 meters long. Further, the induced fractures 101 may be spaced a distance 192 apart from each other. The distance 192 (e.g., 25 meters, 5 meters, 12 meters) may be optimized based on the permeability and the porosity of the rock matrix 162 of the subterranean formation 110.

The induced fractures 101 create a volume 190 within the subterranean formation 110 where the rock matrix 162 of the subterranean formation 110 is connected to the high conductivity fractures 101 located a short distance away. In addition to different configurations of the fractures 101, other factors that may contribute to the viability of the subterranean formation 110 may include, but are not limited to, permeability of the rock matrix 162, capillary pressure, and the temperature and pressure of the subterranean formation 110. Each fracture 101, whether induced or naturally occurring, is defined by a wall 102, also called a frac face 102 herein. The frac face 102 provides a transition between the paths formed by the rock matrices 162 in the subterranean formation 110 and the fracture 101. The subterranean resources 111 flow through the paths formed by the rock matrices 162 in the subterranean formation 110 into the fracture 101.

The rock matrices 162, as well as the rest of the subterranean formation 110, both without and outside the volume 190, have a certain amount of produced water 147 therein. The produced water 147 may be or include, for example, formation water from the formation matrix within the volume 190, moveable free formation water, and "external" water from non-targeted formation/sources (e.g., outside the target volume 190). These sources of produced water 147 may include water from nearby SWD wells. The produced water 147 may migrate from outside a target volume 190 through other fractures, faults, lineaments, other features of the subterranean formation 110, or any combination thereof.

The produced water 147 may have any of a number of different components (e.g., minerals, chemical additives, acids, completion brine) in addition to formation water. The contents of produced water 147 in one part (e.g., outside the volume 190) of the subterranean formation 110 may be the same as, or different than, the contents of the produced water 147 in other parts (e.g., in the rock matrices 162) of the subterranean formation 110. In some cases, such as during a stage (e.g., a hydraulic fracturing stage) of a field operation, the fluids (e.g., fracturing fluid) used in that stage may mix with or include the produced water 147, thereby changing the contents or composition of the in situ water chemistry in parts (e.g., at or near the fractures 101) of the subterranean formation 110. The produced water 147 may include one or more of a number of types of water, including but not limited to sea water, brackish water, flowback or produced water, wastewater (e.g., reclaimed or recycled), brine (e.g., reservoir or synthetic brine), fresh water (e.g., fresh water comprises <1,000 ppm TDS), any other type of water, or any combination thereof.

Figure 3:
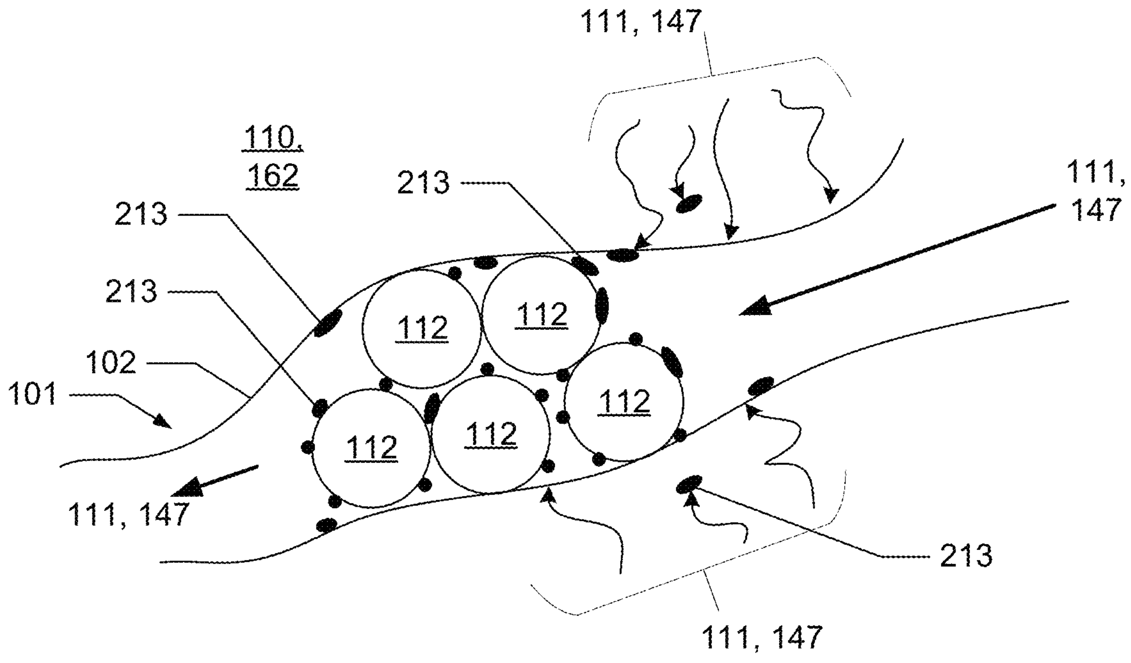
FIG. 3 shows the detail of FIG. 2 at a subsequent point in time according to certain example embodiments.

FIG. 2 shows the detail of FIG. 1D at a subsequent point in time relative to the time captured in FIG. 1D. FIG. 3 shows the detail of FIG. 2 at a subsequent point in time relative to the time captured in FIG. 2. For example, FIG. 2 may show the detail of FIG. 1D six months later (e.g., at the initial stage when the well is put on production) than the time captured in FIG. 1D after flowing a fluid (e.g., a fluid that includes the produced water 147) therethrough, and FIG. 3 may show the detail of FIG. 2 three months later than the time captured in FIG. 2 after continuing to flow the fluid therethrough. Referring to FIGS. 1A through 3, the detail in FIG. 2 shows, in addition to the proppant 112 within the fracture 101, produced water 147 and/or another subterranean resource 111 (e.g., natural gas, oil) flowing within the fracture 101 from the rock matrix 162, around the proppant 112 in the fracture 101, and on to the wellbore 120. In some cases, the subterranean resource 111 is co-present or mixed with the produced water 147.

As the produced water 147 and the other subterranean resource(s) 111 flows within the paths formed by the rock matrices 162 and around the proppant 112 in the fracture 101, scale depositions 213 may occur (e.g., scale particles formed during the shut-in stage before the well is put on production) within the rock matrices 162, on the proppant 112, and/or on the frac face 102. Specifically, components of the produced water 147, such as one or more types of multi-valent cations and/or other types of solid-generating components, may form the basis of the scale depositions 213 and/or other solid accumulations. Over time, the scale depositions 213 may begin to accumulate on the rock matrices 162, on the proppant 112, and/or on the frac face 102. Each of the scale depositions 213 may be an inorganic deposit from ionic materials in water (e.g., the produced water 147) that attaches to solid surfaces. Hydrocarbons may be adsorbed on scale depositions 213. Under field conditions, scale depositions 213 may be a mixture of inorganic and organic components.

Scale depositions 213 may be initiated during a prior phase (e.g., completion) of a field operation, where fluids and chemicals used downhole may interact with formation rock (e.g., the frac face 102, the rock matrices 162) and comingle with the produced water 147 in and/or near perforations and along the fractures 101, resulting in the mobilization and release of elements from the rock matrices 162 adjacent to the fractures 101. Later, in a subsequent phase (e.g., shutting in) of the field operation, the rock-fluid interaction and the commingling of different fluids may lead to the formation (crystallization) and growth of scale depositions 213 in or near the perforations, the rock matrices 162, and the fractures 101. In yet another subsequent phase (e.g., production) of the field operation, the degradation in the conductivity and production flow path over time in the rock matrices 162 and the fractures 101, caused by agglomerate build-up of scale depositions 213, may lead to plugging in or near the perforations, rock matrices 162, fractures 101, and completion tools.

The scale depositions 213 that accumulate within the rock matrices 162 and the fractures 101 may be composed of one or more of any of a number of compounds, including but not limited to calcium carbonate ($CaCO_3$), barium sulfate ($BaSO_4$), calcium sulfate ($CaSO_4$), strontium sulfate ($SrSO_4$), iron carbonate ($FeCO_3$), iron oxide ($Fe_2O_3$), iron sulfide (FeS), zinc sulfide (ZnS), other oxides, other sulfides, other carbonates, other sulfates, halides, and hydroxides. At least some of these compounds involve multi-valent cations found in the produced water 147. Scale depositions 213 may additionally or alternatively be composed of other compounds (e.g., gas hydrates, organic deposits (e.g., asphaltenes, waxes, acid induced accumulations), and naphthanates). The scale depositions 213 may be caused by one or more of any of a number of factors, including but not limited to supersaturation, mixing incompatible ions, changes in temperature, changes in pressure, and a change in the pH of water in the fluid.

Scale depositions 213 may form during the shut-in stage prior to the well being put into production, as shown in FIG. 2. In such a case, the scale depositions 213 disposed on the rock matrices 162, on the proppant 112, and on the frac face 102 are small and spotty. As a result, the scale depositions 213 may not significantly impact the flow of the subterranean resource 111 through the paths within the rock matrices 162 and around the proppant 112 within the fracture 101 formed by the frac face 102. In the portion of the fracture 101 shown at the time captured in FIG. 2, there are 2 separate scale depositions 213 within the rock matrices 162, 8 scale depositions 213 on the proppant 112, and 4 scale depositions 213 on the frac face 102. The number, size, and location of the scale depositions 213 within the rock matrices 162 and the fracture 101 may vary.

When the well is put on production, some scale depositions 213 may stay at their original position, while some scale particles may move/migrate together with the produced water 147 and deposit at another location along the production pathway. As more produced water 147 is produced, the existing scale depositions 213 may increase in size and/or new scale depositions 213 may develop over time. An example of this is captured in FIG. 3, which shows that the scale depositions 213 become larger and less spotty. As a result, the scale depositions 213 in FIG. 3 begin to contribute to inhibit the flow of the produced water 147 and/or other subterranean resources 111 (e.g., hydrocarbons) along the paths formed by the rock matrices 162, through the frac face 102 (impacting migration of the produced water 147 and/or other subterranean resources 111 from the rock matrix 162), and around the proppant 112 (combined with the scale depositions 213 on the proppant 112 and on the frac face 102) within the fractures 101.

As a result, scale depositions 213 may cause a decrease (in some cases, a significant decrease) in well productivity and estimated ultimate recovery (EUR) for the well. Similarly, if the well is used for SWD, the scale depositions 213 (e.g., from injection water, with flow via wellhead to wellbore and formation) may clog or restrict the flow paths into the subterranean formation 110, thereby limiting the useful capacity of the SWD well. In the portion of the fracture 101 shown at the time captured in FIG. 3, there are 25 separate scale depositions 213 within the rock matrices 162, at the frac face 102, and on the proppant 112, many of which are larger (in some cases, significantly larger) than the size of the scale depositions 213 shown in FIG. 2. Also, some of the scale depositions 213 in FIG. 3 have migrated to a new location relative to their location in FIG. 2. Again, the number, size, and location of the scale depositions 213 within the fracture 101 may vary.

In field operations, different chemical additives may be introduced to fluids that are pumped into the wellbore (e.g., wellbore 120). For example, scale inhibitor and/or other chemical agents (e.g., biocide) are commonly included in frac fluid to inhibit/control mineral scale depositions (a form of scale depositions 213) during hydraulic fracturing operations. As frac fluid is injected into the subsurface, it may interact with the frac face 102, proppant, rock matrices, produced water 147, and other elements in the volume 190. Rock-water interaction and fluid commingling may potentially lead to increased risk of scale depositions 213 and solid formation (e.g., create other types of blockage in the fractures 101), leading to adverse effects (e.g., create other types of blockage in the fractures 101) on production performance. In some cases, scale inhibitor and/or other chemical additives may lead to increased risk in the development of scale depositions 213, corrosion, incompatibility, and other production issues.

As another example, injection gas may be used for EOR of a wellbore (e.g., wellbore 120, wellbore 220). Injected gas for EOR may have any of a number of compositions, including but not limited to $CO_2$, $N_2$, and produced gas, where the produced gas (a form of subterranean resource 111) may include hydrocarbon compositions (e.g., $CH_4$, $C_2H_6$, $C_3H_8$, $C_4H_{10}$, $C_5H_{12}$, and $C_6H_{14}$) and/or acidic components (e.g., $CO_2$, $H_2S$). Acidic gas components, such as $CO_2$ and $H_2S$, may dissolve and chemically react in the aqueous phase, which may lead to a change in water chemistry (e.g., in-situ pH) of the produced water 147 and promote rock-water interaction (e.g., mineral dissolution/transformation/precipitation) at the subsurface. The acidic gas-water-rock interaction may potentially lead to increased porosity and permeability of the impacted formation, which may consequently lead to improved oil recovery. At the same time, the acidic gas-water-rock interaction may also lead to mineral trapping of $CO_2$ and a change in production risks, including but not limited to the formation of scale/asphaltene depositions 213 at the subsurface. The acidic gas compositions included in injection gas may potentially lead to elevated $CO_2$ in the produced gas and potential need to decrease the $CO_2$ in produced gas prior to sale. Such factors may be considered for the gas EOR project optimization and economic assessment.

It is important to optimize scale management, asphaltene management, and other factors at the subsurface over time during multiple field operations, which in example embodiments includes, for example, selecting an optimal or recommended injection gas among a number of different injection gas for a given composition of produced water 147 and rock at the subsurface and determining the appropriate concentration of the optimal or recommended injection gas for a given composition of produced water 147 and rock at the subsurface. The recommended injection gas may lead to increased/optimized recovery of other subterranean resources 111 from the subterranean formation 110 or to increase/optimize storage capability of a SWD well within the subterranean formation 110.

Example embodiments are designed to optimize a field operation comprising a gas injection (e.g., EOR) such as by recommending an injection gas to be used during one or more field operations. The recommended injection gas may be determined based on the composition and analysis of the produced water 147 (or other type of water) and the rock at the subsurface by taking visual observations and/or analyzing the post-reaction composition when the recommended injection gas, the produced water 147 (or other type of water), and the rock are mixed. These tests may be conducted at any pressure, at any temperature, and for any length of time. Also, these tests may contain different types of chemical additives (e.g., scale inhibitors, surfactants, corrosion inhibitors) and/or metal components in the aqueous phase. The recommended injection gas, determined using example embodiments, may be used in EOR and/or other field operations (e.g., for fracturing, for SWD) with reduced, little, or no risk of scale depositions 213 developing. In this way, the recommended injection gas may enhance production of the subterranean resource 111 within the volume 190. When water with the recommended injection gas using example embodiments is used for injection into SWD wells, the injectivity and performance of the SWD well may potentially be improved due to the lower/no scaling risk and potential permeability increase due to interaction between rock and the recommended injection gas.

Figure 4:
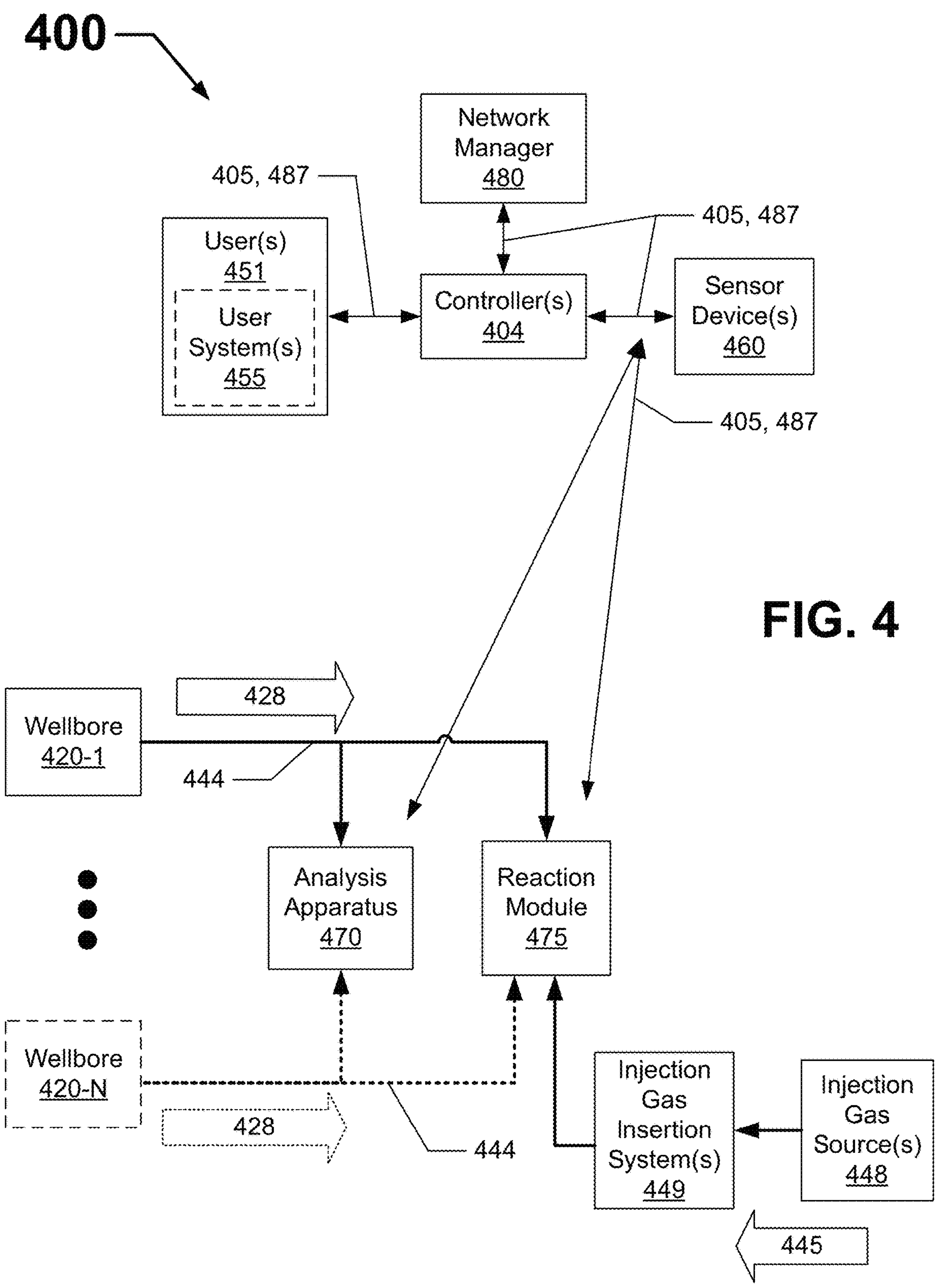
FIG. 4 shows a diagram of a system for improving a field operation that includes a gas injection according to certain example embodiments.

FIG. 4 shows a diagram of a system 400 for enhancing hydrocarbon recovery via gas injection for improved production performance according to certain example embodiments. The system 400 of FIG. 4 includes one or more injection gas sources 448, one or more injection gas insertion systems 449, a reaction module 475, an analysis apparatus 470, one or more wellbores 420 (e.g., wellbore 420-1, wellbore 420-N), one or more controllers 404, one or more sensor devices 460, one or more users 451 (including one or more optional user systems 455), a network manager 480, and a conveyance system 444.

The components shown in FIG. 4 are not exhaustive, and in some embodiments, one or more of the components shown in FIG. 4 may not be included in the example system 400. Any component of the system 400 may be discrete or combined with one or more other components of the system 400. Also, one or more components of the system 400 may have different configurations. For example, one or more sensor devices 460 may be disposed within or disposed on other components (e.g., the conveyance system 444, the analysis apparatus 470, the reaction module 475). As another example, a controller 404, rather than being a stand-alone device, may be part of one or more other components (e.g., the analysis apparatus 470, the reaction module 475) of the system 400.

Referring to FIGS. 1 through 4, the system 400 may have one or more wellbores 420 (e.g., wellbore 420-1, wellbore 420-N). In this case, there may optionally be N wellbores 420. Each wellbore 420 of the system 400 may be substantially the same as the wellbores discussed above with respect to FIGS. 1A and 1B. When there are multiple wellbores 420, two or more wellbores 420 may be from a common pad and/or from different pads. Also, when there are multiple wellbores 420, each wellbore 420 may have characteristics (e.g., total depth, total vertical depth, total length, number of casing stages, size of each casing stage, subterranean formations that are traversed) that may be the same as of different than the characteristics of one or more of the other wellbores 420.

When a sample 428 is taken from a wellbore 420, each sample 428 is taken from a wellbore 420 (e.g., wellbore 420-1) and at a known depth (e.g., 5600 feet of true vertical depth (TVD)) or range of depths (e.g., between 1200 feet and 1400 feet of wellbore depth). A range of depths of a sample 428 collected from a wellbore 420 may correspond to a type of geological formation (e.g., shale, sandstone, carbonate) within a subterranean formation (e.g., subterranean formation 110). The wellbore 420 and depth may be parameters of a sample 428. These parameters may be measured or obtained during a field operation at the time that a sample 428 is initially collected or otherwise acquired adjacent to the wellbore 420. In addition to measurements, a value of a parameter may be obtained through calculations, model results, curves, plots, etc.

Each sample 428 may also yield values (e.g., measurements, calculations, model results, curves, plots, etc.) for a number of additional parameters that may be determined (e.g., measured, modeled, calculated, plotted, etc.) using the analysis apparatus 470, as discussed below. At least some of these additional parameters that are determined using the analysis apparatus 470 are fluid chemistry parameters (e.g., oil chemistry parameters). Examples of fluid chemistry parameters may include outputs of analysis performed using equipment such as, but are not limited to, an oil/gas chromatograph, gas chromatograph-mass spectrometry (GC-MS), a stable carbon isotope analysis, a stable sulfur isotope analysis, SARA, a sulfur analysis, a Ni/V analysis, a DNA sequencing analysis, a water chemistry analysis (e.g., ICP-OES, IC), an alkylbenzene analysis, and a 2D/3D GC-MS.

Examples of some parameters/factors under consideration may include, but are not limited to, temperature, pressure, concentrations of dissolved cations and anions in the aqueous phase at the subsurface, downhole water pH before gas injection, rock mineralogy (e.g., composition of carbonate minerals such as dolomite and calcite), rock fabrics, gas-oil ratio (GOR), water cut, fluid cross flow, original oil in place (OOIP), and oil recovery efficiency. In some cases, values may be obtained (e.g., measurements may be made) for multiple (e.g., more than 50,000) parameters from a single sample 428.

A sample 428 may be in solid form, liquid form, condensate form, and/or gaseous form. In addition to having one or more of a number of various forms, a sample 428 may originate from any of a number of locations (e.g., a wellhead, a surface facility, a subterranean formation). For example, a sample 428 may be in fluid form taken from a wellhead. As another example, a sample 428 may be in fluid form taken from a surface facility. As yet another example, a sample 428 may be in fluid form taken from a subterranean formation. As still another example, a sample 428 may be in solid form (e.g., a rock sample) taken from a subterranean formation.

Each sample 428 is delivered (e.g., from the wellbores 420) to the analysis apparatus 470 using the conveyance system 444. The conveyance system 444 may include any equipment and/or modes of transport so that the samples 428 are delivered to the analysis apparatus 470 in a condition that allows multiple parameters associated with the samples 428 to be determined (e.g., measured). The conveyance system 444 may include any equipment that may transport a sample 428, regardless of the state (e.g., solid, liquid, gas, a combination thereof) of the sample 428. Similarly, the conveyance system 444 may include any equipment that may transport an injection gas 445, regardless of the state (e.g., solid, liquid, gas, a combination thereof) of the injection gas 445.

Examples of such equipment may include, but are not limited to, pipes, tubes, valves, storage tanks, pumps, motors, controllers (e.g., controller 404), sensor devices (e.g., sensor device 460), conveyor belts, trucks, rail systems, shipping containers, refer containers, compressors, cranes, test tubes, heaters, coolers, refrigerants, preservatives, and beakers. Some or all of the conveyance system 444 may be controlled by one or more of the controllers 404. In addition, or in the alternative, some or all of the conveyance system 444 may be controlled by one or more of the users 451, which may include one or more of the user systems 455.

For example, in order to transport liquids and gases within the system 400, the conveyance system 444 may include piping. In such a case, the piping may include multiple pipes, ducts, elbows, joints, sleeves, collars, and similar components that are coupled to each other (e.g., using coupling features such as mating threads) to establish a network for transporting such liquids and/or gases within the system 400. Each component of the piping (as well as other parts of the conveyance system 444) may have an appropriate size (e.g., inner diameter, outer diameter) and be made of an appropriate material (e.g., steel, PVC) to safely and efficiently handle the pressure, temperature, flow rate, and other characteristics of the materials (e.g., solids, liquids, and/or gases) that flow therethrough. As another example, in order to transport solids within the system 400, the conveyance system 444 may include conveyer belts, trucks, bulldozers, backhoes, and/or other similar equipment.

There may be a number of valves placed in-line with the conveyance system 444 (or portions thereof) at various locations in the system 400 to control the flow of the injection gases 445 and the samples 428. A valve may have one or more of any of a number of configurations, including but not limited to a guillotine valve, a ball valve, a gate valve, a butterfly valve, a pinch valve, a needle valve, a plug valve, a diaphragm valve, and a globe valve. One valve may be configured the same as or differently compared to another valve in the system 400. Also, one valve may be controlled (e.g., manually by a user 451, automatically by the controller 404) the same as or differently compared to another valve in the system 400.

The analysis apparatus 470 is configured to perform multiple functions with respect to each of the samples 428, including understanding one or more chemistry factors of a wellbore 420. Utilizing such fluid (e.g., water, oil, gas) chemistry surveillance of the samples 428 may lead to a better understanding of well-well communication, water commingling, subsurface water migration, and/or other related issues and recovery mechanisms associated with gas injection. When a sample 428 is or includes water, the water may be any type of water, including but not limited to produced water (e.g., produced water 147), sea water, brackish water, wastewater (e.g., reclaimed or recycled), brine (e.g., reservoir or synthetic brine), fresh water (e.g., fresh water comprises <1,000 ppm TDS), and/or any other type of water.

For example, the analysis apparatus 470 may be configured to receive each sample 428 delivered by the conveyance system 444. As another example, the analysis apparatus 470 may be configured to determine (e.g., measure, model, calculate), using one or more sensor devices 460, one or more parameters associated with each sample 428. As yet another example, the analysis apparatus 470 may be configured to organize, using one or more of the controllers 404, the values of the parameters associated with each sample 428. As still another example, the analysis apparatus 470 may be configured to analyze, using one or more of the controllers 404, the values of the parameters associated with the samples 428. Such analyses may be used to suggest or recommend one or more injection gases 445, including concentrations thereof, for use in the reaction module 475 along with the samples 428.

Examples of some of the information that may be measured and/or otherwise determined by the analysis apparatus 470 may include, but are not limited to, a percentage of $CO_2$ and $H_2S$ in samples 428 that are or include produced gas when a wellbore 420 is an injector well or an offset well, chemistry surveillance data of a sample 428 that is or includes produced fluids including both water (e.g., produced water 147) and hydrocarbons, subsurface water/oil chemistry homogeneity and connectivity of wellbores 420 of samples 428 that are or include produced water, formation water, oil and gas samples, mineralogy, temperature, and/or pressure of the subterranean formation (e.g., subterranean formation 110) within a volume (e.g., volume 190), a baseline in situ pH and/or scaling/solid formation potential, and characterization of samples 428 that are or include liquid hydrocarbons (e.g., using SARA). Stable isotope analysis and/or other techniques may also be used.

The analysis apparatus 470 may include one or more of a number of other components. Such other components may include, but are not limited to, one or more controllers (e.g., controllers 404), one or more sensor devices (e.g., sensor devices 460), a testing vessel, a motor, a pump, a compressor, tubing, piping, a valve, a heater, a cooling device, and a compressor. In some cases, the analysis apparatus 470 may be configured to simulate downhole conditions. The analysis apparatus 470 may be configured to process multiple samples 428 simultaneously.

The analysis apparatus 470 may be at a single location or spread over multiple locations. Examples of a location for the analysis apparatus 470 (or portion thereof) may include, but are not limited to, a lab on a land-based rig of above the wellbore 420, a lab on a topside of a floating platform above the wellbore 420, and a lab located remotely from the site of the wellbore 420. Some or all of the analysis apparatus 470 may be controlled by one or more of the controllers 404. In addition, or in the alternative, some or all of the analysis apparatus 470 may be controlled by one or more of the users 451, which may include one or more of the user systems 455.

The analysis apparatus 470 of the system 400 (or portions thereof) may be used as a testing environment (e.g., to test the content and characteristics of one or more samples 428) and/or as part of a field trial or field application. As a result, the analysis apparatus 470 of the system 400 may control one or more variables (e.g., pressure, temperature, flow rate) so that one or more of the samples 428 may be tested under certain conditions (e.g., downhole conditions). As such, the analysis apparatus 470 (or portions thereof) may be designed to subject one or more of the samples 428 to conditions (e.g., pressure, temperature, flow rate) that simulate the conditions at the subsurface (e.g., corresponding downhole conditions of the fractures 101 and rock matrix in the subterranean formation 110 adjacent to the wellbore 120).

The system 400 may include one or more injection gas sources 448. Each injection gas source 448 may hold an injection gas 445. Examples of an injection gas source 448 may include, but are not limited to, a tank, an ambient environment, a hose, a test tube, a column, a wellbore 420, a processing system, and a beaker. Each injection gas 445 may have any composition, including but not limited to $CO_2$, $N_2$, $H_2S$, and/or one or more hydrocarbon compositions (e.g., $CH_4$, $C_2H_6$, $C_3H_8$, $C_4H_{10}$, $C_5H_{12}$, and $C_6H_{14}$). When an injection gas 445 is $CO_2$, the injection gas source 448 may be or include underground rock. For example, with coal gasification, injecting air (or oxygen) and steam into an underground oil/gas reservoir or coal bed may result in substantially simultaneously producing $H_2$ and $CO_2$. In such a case, the $H_2$ may be separated (e.g., using membrane technology), and the remaining syngas may be a source of $CO_2$ for use as an injection gas 445. In some cases, such an underground oil/gas reservoir or coal bed may be located proximate to gas EOR fields to simplify transportation logistics of the $CO_2$ as an injection gas 445.

An injection gas 445 is moved from each injection gas source 448 toward the reaction module 475 using one or more injection gas insertion systems 449 in conjunction with the conveyance system 444. Each injection gas insertion system 449 is configured to extract injection gas 445 from an injection gas source 448 and push the injection gas 445 toward the reaction module 475. An injection gas 445 may have one or more of a number of states, including but not limited to a gaseous state, a solid state, a liquid state, or any combination thereof.

The number of injection gas insertion systems 449 in the system 400 may vary. In some embodiments, there may be one injection gas insertion system 449 for each injection gas source 448. In alternative embodiments, there may be one injection gas insertion system 449 for multiple injection gas sources 448. Each injection gas insertion system 449 may include one or more of a number of pieces of equipment to perform its function. Examples of such equipment may include, but are not limited to, a compressor, a motor, a pump, piping (part of the conveyance system 444), a valve, a controller (e.g., controller 404), and a sensor device (e.g., sensor device 460). Some or all of the injection gas insertion system 449 may operate using a controller 404. In addition, or in the alternative, one or more users 451 may perform one or more of the various functions required to move some or all of the injection gas 445 using the injection gas insertion system 449.

The reaction module 475 of the system 400 (or portions thereof) may be used as a testing environment (e.g., to test the interaction of an injection gas 445 with a sample 428 from a wellbore 420, to test the effects of a particular injection gas 445 in a field operation in a wellbore 420) and/or as part of a field trial or field application. As a result, the reaction module 475 of the system 400 may control one or more variables (e.g., pressure, temperature, flow rate) so that one or more of the samples 428 and/or one or more of the injection gases 445 may be tested under certain conditions (e.g., downhole conditions). As such, the reaction module 475 (or portions thereof) may be designed to subject the injection gases 445 and/or one or more of the samples 428 to conditions (e.g., pressure, temperature, flow rate) that simulate the conditions at the subsurface (e.g., corresponding downhole conditions of the fractures 101 and rock matrix in the subterranean formation 110 adjacent to the wellbore 120). Some or all of the reaction module 475 may be controlled by one or more of the controllers 404. In addition, or in the alternative, some or all of the reaction module 475 may be controlled by one or more of the users 451, which may include one or more of the user systems 455.

Whether inside the reaction module 475 or in a collection area (e.g., a header, a manifold) that is upstream of the reaction module 475, an injection gas 445 and a sample 428 are introduced to each other. If the injection gas 445 and the sample 428 are introduced to each other upstream of the reaction module 475, then the combined product is formed in a collection area. In either case, the reaction module 475 mixes the combined product, which is then tested, measured, and/or otherwise determined within the reaction module 475. In certain example embodiments, the reaction module 475 may be configured to provide access to (e.g., expel via a port in the reaction module 475, place into/onto part of the conveyance system 444 that enters the reaction module 475) the injection gases 445 and/or the samples 428.

Conditions (e.g., temperature, pressure) in some or all of the reaction module 475 may vary and may be customized to represent field operating conditions, with temperature and pressure ranging from ambient conditions up to elevated conditions (e.g., 50° F.-150° F. for temperature, 50° F.-100° F. for temperature, 100° F.-150° F. for temperature, 30 psia-200 psia for pressure, 30 psia-110 psia for pressure, 60 psia-120 psia for pressure, 95 psia-200 psia for pressure).

The amount of the injection gas 445 and the sample 428 that are released or withdrawn from the injection gas source (s) 448 and the wellbore(s) 420, respectively, may be regulated in real time. This regulation may be performed automatically by a controller 404 and/or manually by a user 451

(which may include an associated user system 455). This regulation may be performed using equipment such as the conveyance system 444, the one or more injection gas insertion systems 449, valves, regulators, sensor devices 460, etc. An injection gas 445 of an injection gas source 448 and a sample 428 from a wellbore 420 may have any of a number of different compositions that are naturally occurring or man-made.

The reaction module 475 of the system 400 is configured to mix one or more injection gases 445 and one or more samples 428 together. The reaction module 475 may take one or more of any of a number of forms, including but not limited to a column, a test tube, a chamber, some type of mixer (e.g., a centrifuge mixer, a desander, a tumbler mixer, a homogenizer, a static mixer, a drum mixer, a fluidization mixer, agitator mixers, paddle mixers, an emulsifier, a drum mixer, a pail mixer, a convective mixer, an agitator, a batch mixer, a ribbon mixer), and/or some other vessel. In some cases, as when assessing or validating field trials, field deployment, field surveillance, and/or field optimization, the reaction module 475 may be a wellbore 420 (or portion thereof). The reaction module 475 may include one or more of a number of features used to mix and/or otherwise cause a reaction between an injection gas 445 and a sample 428. The reaction module 475, may operate substantially continuously (as when an injection gas 445 and/or a sample 428 substantially continuously flow into the reaction module 475) or at intervals (as when an injection gas 445 and/or a sample 428 are introduced into the reaction module 475 intermittently).

The reaction module 475 may be or include a single apparatus (with or without multiple portions) or multiple apparatus (or portions thereof) that operate in series and/or in parallel with each other. As an example, the reaction module 475 may include a temperature conditioning portion, a mixing portion, a drying portion, and a separating portion that operate in series with each other. As another example, the reaction module 475 may include multiple mixers that operate in parallel with each other, where each mixer may mix a different combination of injection gases 445 and samples 428 simultaneously.

The reaction module 475 may include one or more of a number of pieces of equipment to perform these functions. Examples of such pieces of equipment may include, but are not limited to, a vessel, a funnel, a strainer, a separator, an agitator, a paddle, a circulating system, an aerator, a vibrating mechanism, a centrifuge, a motor, a pump, a compressor, piping, a valve, a controller (e.g., controller 404), and a sensor device (e.g., sensor device 460). The various parts of the reaction module 475 are configured (e.g., made of the proper material) to withstand the conditions (e.g., pressure, temperature, acidity, alkalinity) simulated by the reaction module 475.

Some or all of the reaction module 475 may operate using a controller 404. In addition, or in the alternative, one or more users 451 (e.g., a human being) may control some or all of the various functions performed by the reaction module 475. In some cases, some or all of the reaction module 475 may be paused or stopped so that the injection gases 445, the samples 428, the combined product of the injection gases 445 and the samples 428, the byproducts that result from reactions between the injection gases 445 and the samples 428, and/or any other suitable components may be evaluated.

In certain example embodiments, when the samples 428 include rock and water (e.g., formation water 147) from the subterranean formation 110, the reaction module 475 may be used to assess the interaction between an injection gas 445 (e.g., gas containing a certain concentration of $CO_2$ or $H_2S$ and other components), the rock, and the water, as well as the resulting impact of that interaction. For example, the reaction module 475 may include an Amott cell and scanning electron microscopy with energy dispersive x-ray analysis (SEM/EDX) equipment, which may be used to study the impact of water chemistry and acidic gas (e.g., $CO_2$) on oil recovery (e.g., using the Amott cell) and rock surface/pore structures (e.g., using the SEM/EDX equipment).

As another example, when the samples 428 include rock and water (e.g., formation water 147) from the subterranean formation 110, the reaction module 475 may be used to assess the impact (e.g., actual, potential) of the interaction between an injection gas 445 (e.g., an acidic gas like $CO_2$), the water, and the rock on production risks, including but not limited to scale and asphaltene deposition 213 and set up mitigation/control strategies. In such cases, chemical additives (e.g., scale inhibitor) may be included in the tests to assess its effectiveness and optimal dosage to mitigate risk and optimize oil recovery. As yet another example, the reaction module 475 may be used to estimate optimized compositions of an injection gas 445 (e.g., a gas stream containing a certain concentration of $CO_2$) based on targeted formation pressure within a wellbore 420, water chemistry, and other considerations (e.g., corrosion control).

As still another example, based on the data/results obtained from the analysis apparatus 470, the reaction module 475 may be used to conduct modeling/simulation to predict how an injection gas (e.g., a gas stream containing a certain concentration of $CO_2$) with different concentrations, water chemistry, and targeted formation pressure impact the in-situ water pH, rock-water interaction, and/or other factors that may impact recovery of the subterranean resources 111. Some examples of $CO_2$-water-rock chemistry interactions, where the $CO_2$ is an injection gas 445, may include, but are not limited to, the following reaction formulas:

$$CO_2 + H_2O \leftrightarrow H_2CO_3 \leftrightarrow H^+ + HCO_3^- \quad (1)$$

$$CaMg(CO_3)_2(\text{Dolomite}) + 2H^+ \leftrightarrow Ca^{2+} + Mg^{2+} + 2HCO_3^- \quad (2)$$

$$CaNa_4Al_6Si_{14}O_{40}(\text{Oligoclase}) + 6H^+ + 34H_2O \leftrightarrow Ca^{2+} + 4Na^+ + 6Al(OH)_3 + 14H_4SiO_4 \quad (3)$$

$$Ca^{2+} + HCO_3^- \leftrightarrow CaCO_3(\text{Calcite}) + H^+ \quad (4)$$

In certain example embodiments, the reaction module 475 may be used in field trials, field deployment, field surveillance, field optimization, and/or other applications. For example, the reaction module 475 may be used to monitor the insertion/injection of an injection gas 445 and/or the production profile during an EOR operation. As another example, the reaction module 475 may be used to monitor the chemistry of the produced water (e.g., produced water 147) and/or the composition of produced subterranean resources 111 (e.g., hydrocarbons).

As yet another example, the reaction module 475 may be used to investigate the impact of the interaction between an injection gas 445, aqueous phase, hydrocarbon phase, and rock and inter-well fluid migration based on fluid (e.g., water, hydrocarbon) chemistry data and/or production data (e.g., water rates, pressure data). As still another example, the reaction module 475 may be used to monitor and assess fluid chemistry-related production risks, including but not limited to scale accumulation 213, corrosion, and asphaltene. As yet another example, the reaction module 475 may be used to assess mineral trapping of $CO_2$ and/or mass balance.

As still another example, the reaction module 475 may be used to assess the overall impact on EOR, well performance, mineral trapping of $CO_2$, and/or other performance metrics (e.g., economic assessment/cost/operational cost, impact on product gas specs) based on field results. As yet another example, the reaction module 475 may be used to optimize the concentrations in acidic gas (e.g., $CO_2$) as an injection gas 445, targeted formation pressure, water chemistry (e.g., when gas-water alternating injection is utilized), and/or other parameters in later cycles based on results and learnings from previous cycles.

As a further example, the reaction module 475 may be used to determine the type and/or amount of solid-generating components and/or total dissolved solids (TDSs) within the produced water (e.g., produced water 147. Testing with the reaction module 475 may use historical data and/or field data (e.g., values of measurements from sensor devices 460). Testing using the reaction module 475 may generate test scenarios or expected results. Testing using the reaction module 475 may include the use of process chemistry simulators, fluid electrolyte modeling, chemistry calculations using field/historical data to model the process, etc.

Evaluation of an injection gas 445 by the reaction module 475 may be correlated, directly or indirectly, to whether and how much scale depositions 213 may form in the fractures 101 and rock matrices in the volume 190 of the subterranean formation 110 adjacent to a wellbore 420 when the injection gas 445 is used in one or more field operations, and to how much scale precipitation may be reduced by using the injection gas 445 for a fracturing operation or for injection into a SWD or other type of injection well compared to existing operations. In addition, or in the alternative, the reaction module 475 may be used to alter (e.g., decrease) the pH value of the produced water 147 by adding one or more of a number of injection gases 445 that contain compositions of acidic gas (e.g., $CO_2$, $H_2S$), which may lower the scaling potential with respect to calcite and other types of mineral scales.

The system 400 may include one or more controllers 404. A controller 404 of the system 400 communicates with and in some cases controls one or more of the other components (e.g., a sensor device 460, the analysis apparatus 470, the reaction module 475) of the system 400. A controller 404 performs any of a number of functions that include obtaining and sending data, evaluating data, following protocols, running algorithms, and sending commands. A controller 404 may include one or more of a number of components. As discussed below with respect to FIG. 5, such components of a controller 404 may include, but are not limited to, a control engine, a data organization module, an analysis module, a communication module, a timer, a counter, a power module, a storage repository, a hardware processor, memory, a transceiver, an application interface, and a security module.

When there are multiple controllers 404 (e.g., one controller 404 for one or more injection gas insertion systems 449, another controller 404 for the analysis apparatus 470, yet another controller 404 for the reaction module 475, still another one or more controllers 404 for the conveyance system 444), each controller 404 may operate independently of each other. Alternatively, two or more of the multiple controllers 404 may work cooperatively with each other. As yet another alternative, one of the controllers 404 may control some or all of one or more other controllers 404 in the system 400. Each controller 404 may be considered a type of computer device, as discussed below with respect to FIG. 6.

Each sensor device 460 includes one or more sensors that measure one or more parameters (e.g., pressure, flow rate, temperature, humidity, mass, weight, fluid content, voltage, current, permeability, porosity, rock characteristics, chemical elements in a fluid, chemical elements in a solid). Examples of a sensor of a sensor device 460 may include, but are not limited to, a temperature sensor, a flow sensor, a pressure sensor, a scale, a mass spectrometer (e.g., a quadrupole mass analyzer, a time of flight mass analyzer, a quadrupole ion trap mass analyzers, an electrostatic sector mass analyzer), a chromatograph, a DNA sequencing apparatus, a sulfur analyzer, a voltmeter, an ammeter, a permeability meter, a porosimeter, and a camera. A sensor device 460 may measure a parameter associated with one or more samples 428 (whether in a raw state, during a reaction (e.g., with an injection gas 445), or after a reaction (e.g., with an injection gas 445)), one or more injection gases 445 (whether in a raw state, during a reaction (e.g., with a sample 428), or after a reaction (e.g., with a sample 428)), and/or any byproducts of a reaction between one or more samples 428 and one or more injection gases 445.

A number of different tests may be run using one or more of the sensor devices 460. Such tests may include, but are not limited to, a saturates, aromatics, resins, and asphaltenes (SARA) analysis, a whole oil gas chromatograph analysis, an oil biomarker gas chromatograph-mass spectrometry (GC-MS) analysis, a stable carbon isotope analysis, a stable sulfur isotope analysis, a nickel/vanadium (Ni/V) analysis, DNA sequencing for oil samples, a water analysis, an alkylbenzene analysis, a 2D/3D GC-MS analysis, a gas-oil ratio (GOR) analysis, an oil concentration analysis, a hydrogen sulfide content analysis, an original oil in place (OOIP) analysis, a mixed oil ratio analysis, an oil inflow analysis, and an oil recovery efficiency analysis.

A sensor device 460 may also be used with respect to the conveyance system 444. For example, a sensor device 460 may be configured to measure a parameter (e.g., flow rate, pressure, temperature) of a sample 428 and/or an injection gas 445 at one or more points in the conveyance system 444 of the system at a particular time. As an example, a sensor device 460 may be configured to determine how open or closed a valve within the conveyance system 444 is. As another example, one or more sensor devices 460 may be used to identify the contents of a sample 428 and the concentration of each of the contents within the sample 428. As still another example, one or more sensor devices 460 may be used to identify the contents of an injection gas 445 and/or the concentration of each of the contents within the injection gas 445. In some cases, a number of sensor devices 460, each measuring a different parameter, may be used in combination to determine and confirm whether a controller 404 should take a particular action (e.g., operate a valve, operate or adjust the operation of the analysis apparatus 470). When a sensor device 460 includes its own controller 404 (or portions thereof), then the sensor device 460 may be considered a type of computer device, as discussed below with respect to FIG. 6.

A user 451 may be any person that interacts, directly or indirectly, with a controller 404, a sensor device 460, the analysis apparatus 470, the reaction module 475, and/or any other component of the system 400. Examples of a user 451 may include, but are not limited to, a business owner, an engineer, a company representative, a geologist, a consultant, a drilling engineer, a contractor, and a manufacturer's representative. A user 451 may use one or more user systems 455, which may include a display (e.g., a GUI). A user system 455 of a user 451 may interact with (e.g., send data to, obtain data from) the controller 404 via an application interface and using the communication links 405. The user 451 may also interact directly with the controller 404 through a user interface (e.g., keyboard, mouse, touchscreen).

The network manager 480 is a device or component that controls all or a portion (e.g., a communication network, a controller 404) of the system 400. The network manager 480 may be substantially similar to the controller 404, as described above. For example, the network manager 480 may include a controller that has one or more components and/or similar functionality to some or all of the controller 404. Alternatively, the network manager 480 may include one or more of a number of features in addition to, or altered from, the features of the controller 404. As described herein, control and/or communication with the network manager 480 may include communicating with one or more other components of the same system 400 or another system. In such a case, the network manager 480 may facilitate such control and/or communication. The network manager 480 may be called by other names, including but not limited to a master controller, a network controller, a gateway, and an enterprise manager. The network manager 480 may be considered a type of computer device, as discussed below with respect to FIG. 6.

Interaction between each controller 404, the sensor devices 460, the users 451 (including any associated user systems 455), the network manager 480, and other components (e.g., the conveyance system 444, an injection gas insertion system 449, the analysis apparatus 470, the reaction module 475) of the system 400 may be conducted using communication links 405 and/or power transfer links 487. Each communication link 405 may include wired (e.g., Class 1 electrical cables, Class 2 electrical cables, electrical connectors, Power Line Carrier, RS485) and/or wireless (e.g., Wi-Fi, Zigbee, visible light communication, cellular networking, Bluetooth, Bluetooth Low Energy (BLE), ultra-wide band (UWB), WirelessHART, ISA100) technology. A communication link 405 may transmit signals (e.g., communication signals, control signals, data) between each controller 404, the sensor devices 460, the users 451 (including any associated user systems 455), the network manager 480, and the other components of the system 400.

Each power transfer link 487 may include one or more electrical conductors, which may be individual or part of one or more electrical cables. In some cases, as with inductive power, power may be transferred wirelessly using power transfer links 487. A power transfer link 487 may transmit power between each controller 404, the sensor devices 460, the users 451 (including any associated user systems 455), the network manager 480, and the other components of the system 400. Each power transfer link 487 may be sized (e.g., 12 gauge, 18 gauge, 4 gauge) in a manner suitable for the amount (e.g., 480V, 24V, 120V) and type (e.g., alternating current, direct current) of power transferred therethrough.

Figure 5:
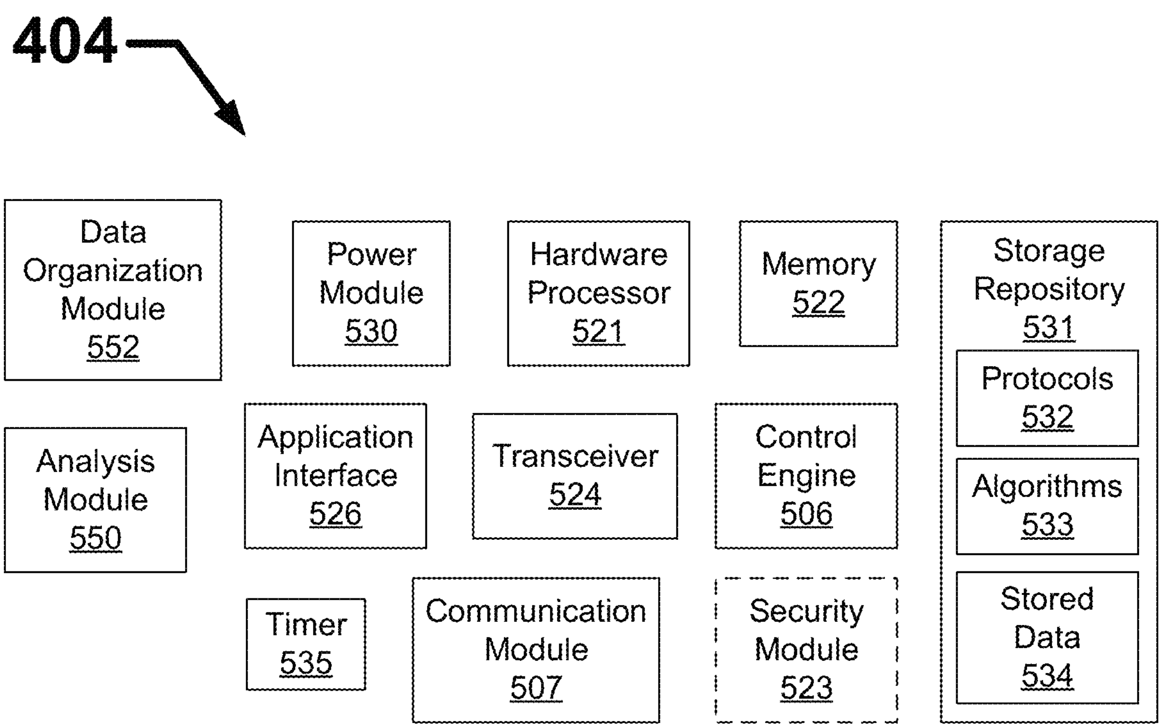
FIG. 5 shows a system diagram of a controller according to certain example embodiments.

FIG. 5 shows a system diagram of a controller 404 according to certain example embodiments. Referring to FIGS. 1A through 5, the controller 404 may be substantially the same as a controller 404 discussed above with respect to FIG. 4. The controller 404 includes multiple components. In this case, the controller 404 of FIG. 5 includes a control engine 506, a data organization module 552, an analysis module 550, a communication module 507, a timer 535, a power module 530, a storage repository 531, a hardware processor 521, a memory 522, a transceiver 524, an application interface 526, and, optionally, a security module 523. A controller 404 (or components thereof) may be located at or near the various components of the system 400. In addition, or in the alternative, the controller 404 (or components thereof) may be located remotely from (e.g., in the cloud, at an office building) the various components of the system 400.

The storage repository 531 may be a persistent storage device (or set of devices) that stores software and data used to assist the controller 404 in communicating with one or more other components of a system, such as the users 451 (including associated user systems 455), each injection gas insertion system 449, the analysis apparatus 470, the reaction module 475, the network manager 480, the sensor devices 460, etc. of the system 400 of FIG. 4 above. In one or more example embodiments, the storage repository 531 stores one or more protocols 532, algorithms 533, and stored data 534.

The protocols 532 of the storage repository 531 may be any procedures (e.g., a series of method steps) and/or other similar operational processes that the control engine 506 of the controller 404 follows based on certain conditions at a point in time. The protocols 532 may include any of a number of communication protocols that are used to send and/or obtain data between the controller 404 and other components of a system (e.g., the system 400). Such protocols 532 used for communication may be time-synchronized protocols. Examples of such time-synchronized protocols may include, but are not limited to, a highway addressable remote transducer (HART) protocol, a wirelessHART protocol, and an International Society of Automation (ISA) 100 protocol. In this way, one or more of the protocols 532 may provide a layer of security to the data transferred within a system (e.g., the system 400). Other protocols 532 used for communication may be associated with the use of Wi-Fi, Zigbee, visible light communication (VLC), cellular networking, BLE, UWB, and Bluetooth.

The algorithms 533 may be any formulas, mathematical models, forecasts, simulations, and/or other similar tools that the control engine 506 of the controller 404 uses to reach a computational conclusion. For example, one or more algorithms 533 may be used, in conjunction with one or more protocols 532, to assist the controller 404 to determine when to start, adjust, and/or stop the operation of the analysis apparatus 470, an injection gas insertion system 449, the reaction module 475, and/or the conveyance system 444. As another example, one or more algorithms 533 may be used, in conjunction with one or more protocols 532, to assist the controller 404 to determine when to have a sensor device 460 measure a value of a parameter and subsequently perform a calculation or make a determination using the value.

As yet another example, one or more algorithms 533 may be used, in conjunction with one or more protocols 532, to assist the controller 404 to identify an optimal (e.g., most cost effective, most likely to optimize an EOR operation) or recommended injection gas 445 based on the composition of a wellbore 420. As still another example, one or more algorithms 533 may be used, in conjunction with one or more protocols 532, to assist the controller 404 in identifying the composition of the samples 428 (e.g., of a wellbore 420). As yet another example, one or more algorithms 533 may be used, in conjunction with one or more protocols 532, to assist the controller 404 in evaluating actual results of using a recommended injection gas 445 in an EOR operation in a wellbore 420 against the anticipated results. An algorithms 533 may be generated based on experimental results, field trial results, and/or other types of modeling/calculation/testing.

Stored data 534 may be any data associated with a field (e.g., the subterranean formation 110, the induced fractures 101 within the volume 190 adjacent to a wellbore 420, the characteristics of proppant 112 used in a field operation, composition of an injection gas 445, nameplate data for equipment in the conveyance system 444, the analysis apparatus 470, and the reaction module 475), other fields (e.g., other wellbores and subterranean formations), values of measurements made by the sensor devices 460, threshold values, tables, results of previously run or calculated algorithms 533, updates to protocols 532, user preferences, and/or any other suitable data. Such data may be any type of data, including but not limited to historical data, present data, and future data (e.g., forecasts). The stored data 534 may be associated with some measurement of time derived, for example, from the timer 535.

Examples of a storage repository 531 may include, but are not limited to, a database (or a number of databases), a file system, cloud-based storage, a hard drive, flash memory, some other form of solid-state data storage, or any suitable combination thereof. The storage repository 531 may be located on multiple physical machines, each storing all or a portion of the communication protocols 532, the algorithms 533, and/or the stored data 534 according to some example embodiments. Each storage unit or device may be physically located in the same or in a different geographic location.

The storage repository 531 may be operatively connected to the control engine 506. In one or more example embodiments, the control engine 506 includes functionality to communicate with the users 451 (including associated user systems 455), the sensor devices 460, the network manager 480, and the other components in the system 400. More specifically, the control engine 506 sends information to and/or obtains information from the storage repository 531 in order to communicate with the users 451 (including associated user systems 455), the sensor devices 460, the network manager 480, and the other components of the system 400. As discussed below, the storage repository 531 may also be operatively connected to the communication module 507 in certain example embodiments.

In certain example embodiments, the control engine 506 of the controller 404 controls the operation of one or more components (e.g., the communication module 507, the timer 535, the transceiver 524) of the controller 404. For example, the control engine 506 may activate the communication module 507 when the communication module 507 is in "sleep" mode and when the communication module 507 is needed to send data obtained from another component (e.g., a sensor device 460) in the system 400. In addition, the control engine 506 of the controller 404 may control the operation of one or more other components (e.g., the analysis apparatus 470, the reaction module 475, an injection gas insertion system 449, the conveyance system 444), or portions thereof, of the system 400.

The control engine 506 of the controller 404 may communicate with one or more other components of the system 400. For example, the control engine 506 may use one or more protocols 532 to facilitate communication with the sensor devices 460 to obtain data (e.g., values of measurements of various parameters, such as temperature, pressure, and flow rate), whether in real time or on a periodic basis and/or to instruct a sensor device 460 to take a measurement. The control engine 506 may use values of measurements of parameters taken by sensor devices 460 while one or more of the samples 428 and one or more of the injection gases 445 are being processed within the reaction module 475, as well as one or more protocols 532 and/or algorithms 533, to determine a proposed injection gas 445 for EOR operations in a wellbore 420.

As yet another example, the control engine 506 may use one or more algorithms 533 and/or protocols 532 to recommend a change to the proposed injection gas 445 (e.g., swapping one injection gas 445 for another injection gas 445, altering the composition and/or source of the proposed injection gas 445, increasing an amount (concentration) of the proposed injection gas, decreasing an amount of an additive) based on the analysis conducted by the reaction module 475 in an attempt to optimize available resources and economics in a particular field operation (e.g., EOR). A number of other capabilities of the control engine 506 (as well as the controller 404 as a whole) are discussed below with respect to FIG. 7.

The control engine 506 of a controller 404 may also use one or more algorithms 533 and/or one or more protocols 532 to receive each sample 428 delivered by the conveyance system 444 (e.g., from a wellbore 420). The control engine 506 of a controller 404 may further use one or more algorithms 533 and/or one or more protocols 532 to allow the analysis apparatus 470 to determine, using one or more sensor devices 460, one or more parameters associated with each sample 428. The control engine 506 of a controller 404 may also use one or more algorithms 533 and/or one or more protocols 532 to allow the analysis apparatus 470 to organize, using one or more of the controllers 404, the values of the parameters associated with each sample 428.

The control engine 506 of a controller 404 may also use one or more algorithms 533 and/or one or more protocols 532 to allow the analysis apparatus 470 to estimate a chemical composition and concentration of one or more injection gases 445 to be combined with the samples 428 for testing. The control engine 506 of a controller 404 may further use one or more algorithms 533 and/or one or more protocols 532 to allow the reaction module 475 to combine one or more injection gases 445 with one or more samples 428. The control engine 506 of a controller 404 may further use one or more algorithms 533 and/or one or more protocols 532 to allow the reaction module 475 to evaluate actual performance of an injection gas 445 when combined with samples 428 relative to predicted performance of the injection gas 445 when combined with samples 428.

The control engine 506 of a controller 404 may also use one or more algorithms 533 and/or one or more protocols 532 to generate a representation of an injection gas 445 and/or a sample 428. The control engine 506 of a controller 404 may further use one or more algorithms 533 and/or one or more protocols 532 to display or otherwise present, or cause to be displayed or otherwise presented, the representation of an injection gas 445 and/or a sample 428 on a display (or other type of I/O device, such as the I/O device 616 as discussed below with respect to FIG. 6).

The control engine 506 may generate and process data associated with control, communication, and/or other signals sent to and obtained from the users 451 (including associated user systems 455), the sensor devices 460, the network manager 480, and the other components of the system 400. In certain embodiments, the control engine 506 of the controller 404 may communicate with one or more components of a system external to the system 400. For example, the control engine 506 may interact with an inventory management system by ordering replacements for components or pieces of equipment (e.g., a sensor device 460, a valve, a motor) within the system 400 that has failed or is failing. As another example, the control engine 506 may interact with a contractor or workforce scheduling system by arranging for the labor needed to replace a component or piece of equipment in the system 400. In this way and in other ways, the controller 404 is capable of performing a number of functions beyond what could reasonably be considered a routine task.

In certain example embodiments, the control engine 506 may include an interface that enables the control engine 506 to communicate with the sensor devices 460, the user systems 455, the network manager 480, and/or other components of the system 400. For example, if a user system 455 operates under IEC Standard 62386, then the user system 455 may have a serial communication interface that will transfer data to the controller 404. Such an interface may operate in conjunction with, or independently of, the protocols 532 used to communicate between the controller 404 and the users 451 (including corresponding user systems 455), the sensor devices 460, the network manager 480, and the other components of the system 400.

The control engine 506 (or other components of the controller 404) may also include one or more hardware components and/or software elements to perform its functions. Such components may include, but are not limited to, a universal asynchronous receiver/transmitter (UART), a serial peripheral interface (SPI), a direct-attached capacity (DAC) storage device, an analog-to-digital converter, an inter-integrated circuit (I2C), and a pulse width modulator (PWM).

The analysis module 550 of the controller 404 may be configured to compare the values (e.g., as measured by one or more of the sensor devices 460) of the various parameters associated with each sample 428 and each injection gas 445. The values assessed by the analysis module 550 may originate in the analysis apparatus 470 or the reaction module 475. The comparisons made by the analysis module 550 may be performed using the control engine 506 in combination with one or more protocols 532 and/or one or more algorithms 533. The comparisons made by the analysis module 550 may include tables generated and maintained by the analysis module 550.

In some cases, the analysis module 550 may also be configured to determine, using the control engine 506 in combination with one or more protocols 532 and/or one or more algorithms 533, a proposed injection gas 445, including a chemical composition and/or a concentration. When this task is complete, the analysis module 550 may communicate the proposed injection gas 445 (e.g., to a user 451, to the network manager 480). The analysis module 550 may further be configured to determine, using the control engine 506 in combination with one or more protocols 532 and/or one or more algorithms 533, how actual performance of the proposed injection gas 445 during a field operation (e.g., an EOR operation) compares to forecast performance of the proposed injection gas 445. To the extent that differences exist between actual and forecast performance of the proposed injection gas 445, the analysis module 550 may make the appropriate adjustments to stored data 534 (e.g., reorganize tables), one or more of the protocols 532, and/or one or more of the algorithms 533 to make future forecasts more accurate.

The analysis module 550 may use any of a number of techniques, protocols 532, algorithms 533, and/or other methods for performing its functions. Such methods may be used to balance a number of goals, such as reducing data, improved accuracy, and performing efficient correlations and pattern finding. Examples of such methods may include, but are not limited to, principal component analysis (PCA), restricted isometry constant (RIC) statistical method, risk management index (RMI) statistical method, artificial intelligence (AI) approaches, and machine learning/deep learning approaches.

The data organization module 552 of the controller 404 may be configured to organize the data (e.g., values of measurements made by the sensor devices 460 of the various parameters associated with the samples 428, the injection gases 445, and the combinations/reactions therebetween, results of algorithms 533) stored in the storage repository 531 of the controller 404. The data organization module 552 may organize the data using the control engine 506 in combination with one or more protocols 532 and/or one or more algorithms 533. The data organization module 552 may organize data in tables and/or in any other format.

The data organization module 552 of the controller 404 may also be configured to purge any data that is determined to be unused. Put another way, values of erroneous measurements and/or values of measurements that are unused in calculations may be purged from the storage repository 531 by the data organization module 552. Purges made by the data organization module 552 may be executed using the control engine 506 in combination with one or more protocols 532 and/or one or more algorithms 533.

The communication module 507 of the controller 404 determines and implements the communication protocol (e.g., from the protocols 532 of the storage repository 531) that is used when the control engine 506 communicates with (e.g., sends signals to, obtains signals from) the user systems 455, the sensor devices 460, the network manager 480, and the other components of the system 400. In some cases, the communication module 507 accesses the stored data 534 to determine which communication protocol is used to communicate with another component of the system 400. In addition, the communication module 507 may identify and/or interpret the communication protocol of a communication obtained by the controller 404 so that the control engine 506 may interpret the communication. The communication module 507 may also provide one or more of a number of other services with respect to data sent from and obtained by the controller 404. Such services may include, but are not limited to, data packet routing information and procedures to follow in the event of data interruption.

The timer 535 of the controller 404 may track clock time, intervals of time, an amount of time, and/or any other measure of time. The timer 535 may also count the number of occurrences of an event, whether with or without respect to time. Alternatively, the control engine 506 may perform a counting function. The timer 535 is able to track multiple time measurements and/or count multiple occurrences concurrently. The timer 535 may track time periods based on an instruction obtained from the control engine 506, based on an instruction obtained from a user 451, based on an instruction programmed in the software for the controller 404, based on some other condition (e.g., the occurrence of an event) or from some other component, or from any combination thereof. In certain example embodiments, the timer 535 may provide a time stamp for each packet of data obtained from another component (e.g., a sensor device 460) of the system 400.

The power module 530 of the controller 404 obtains power from a power supply (e.g., AC mains) and manipulates (e.g., transforms, rectifies, inverts) that power to provide the manipulated power to one or more other components (e.g., the timer 535, the control engine 506) of the controller 404, where the manipulated power is of a type (e.g., alternating current, direct current) and level (e.g., 12V, 24V, 120V) that may be used by the other components of the controller 404. In some cases, the power module 530 may also provide power to one or more of the sensor devices 460.

The power module 530 may include one or more of a number of single or multiple discrete components (e.g., transistor, diode, resistor, transformer) and/or a microprocessor. The power module 530 may include a printed circuit board, upon which the microprocessor and/or one or more discrete components are positioned. In addition, or in the alternative, the power module 530 may be a source of power in itself to provide signals to the other components of the controller 404. For example, the power module 530 may be or include an energy storage device (e.g., a battery). As another example, the power module 530 may be or include a localized photovoltaic power system.

The hardware processor 521 of the controller 404 executes software, algorithms (e.g., algorithms 533), and firmware in accordance with one or more example embodiments. Specifically, the hardware processor 521 may execute software on the control engine 506 or any other portion of the controller 404, as well as software used by the users 451 (including associated user systems 455), the network manager 480, and/or other components of the system 400. The hardware processor 521 may be an integrated circuit, a central processing unit, a multi-core processing chip, SoC, a multi-chip module including multiple multi-core processing chips, or other hardware processor in one or more example embodiments. The hardware processor 521 may be known by other names, including but not limited to a computer processor, a microprocessor, and a multi-core processor.

In one or more example embodiments, the hardware processor 521 executes software instructions stored in memory 522. The memory 522 includes one or more cache memories, main memory, and/or any other suitable type of memory. The memory 522 may include volatile and/or non-volatile memory. The memory 522 may be discretely located within the controller 404 relative to the hardware processor 521. In certain configurations, the memory 522 may be integrated with the hardware processor 521.

In certain example embodiments, the controller 404 does not include a hardware processor 521. In such a case, the controller 404 may include, as an example, one or more field programmable gate arrays (FPGA), one or more insulated-gate bipolar transistors (IGBTs), and/or one or more integrated circuits (ICs). Using FPGAs, IGBTs, ICs, and/or other similar devices known in the art allows the controller 404 (or portions thereof) to be programmable and function according to certain logic rules and thresholds without the use of a hardware processor. Alternatively, FPGAs, IGBTs, ICs, and/or similar devices may be used in conjunction with one or more hardware processors 521.

The transceiver 524 of the controller 404 may send and/or obtain control and/or communication signals. Specifically, the transceiver 524 may be used to transfer data between the controller 404 and the users 451 (including associated user systems 455), the sensor devices 460, the network manager 480, and the other components of the system 400. The transceiver 524 may use wired and/or wireless technology. The transceiver 524 may be configured in such a way that the control and/or communication signals sent and/or obtained by the transceiver 524 may be obtained and/or sent by another transceiver that is part of a user system 455, a sensor device 460, the network manager 480, and/or another component of the system 400. The transceiver 524 may send and/or obtain any of a number of signal types, including but not limited to radio frequency signals.

When the transceiver 524 uses wireless technology, any type of wireless technology may be used by the transceiver 524 in sending and obtaining signals. Such wireless technology may include, but is not limited to, Wi-Fi, Zigbee, VLC, cellular networking, BLE, UWB, and Bluetooth. The transceiver 524 may use one or more of any number of suitable communication protocols (e.g., ISA100, HART) when sending and/or obtaining signals.

Optionally, in one or more example embodiments, the security module 523 secures interactions between the controller 404, the users 451 (including associated user systems 455), the sensor devices 460, the network manager 480, and the other components of the system 400. More specifically, the security module 523 authenticates communication from software based on security keys verifying the identity of the source of the communication. For example, user software may be associated with a security key enabling the software of a user system 455 to interact with the controller 404. Further, the security module 523 may restrict receipt of information, requests for information, and/or access to information.

A user 451 (which may include an associated user system 455), the sensor devices 460, the network manager 480, and the other components of the system 400 may interact with the controller 404 using the application interface 526. Specifically, the application interface 526 of the controller 404 obtains data (e.g., information, communications, instructions, updates to firmware) from and sends data (e.g., information, communications, instructions) to the user systems 455 of the users 451, the sensor devices 460, the network manager 480, and/or the other components of the system 400. Examples of an application interface 526 may be or include, but are not limited to, an application programming interface, a web service, a data protocol adapter, some other hardware and/or software, or any suitable combination thereof. Similarly, the user systems 455 of the users 451, the sensor devices 460, the network manager 480, and/or the other components of the system 400 may include an interface (similar to the application interface 526 of the controller 404) to obtain data from and send data to the controller 404 in certain example embodiments.

In addition, as discussed above with respect to a user system 455 of a user 451, one or more of the sensor devices 460, the network manager 480, and/or one or more of the other components of the system 400 may include a user interface. Examples of such a user interface may include, but are not limited to, a graphical user interface, a touchscreen, a keyboard, a monitor, a mouse, some other hardware, or any suitable combination thereof.

The controller 404, the users 451 (including associated user systems 455), the sensor devices 460, the network manager 480, and the other components of the system 400 may use their own system or share a system in certain example embodiments. Such a system may be, or contain a form of, an Internet-based or an intranet-based computer system that is capable of communicating with various software. A computer system includes any type of computing device and/or communication device, including but not limited to the controller 404. Examples of such a system may include, but are not limited to, a desktop computer with a Local Area Network (LAN), a Wide Area Network (WAN), Internet or intranet access, a laptop computer with LAN, WAN, Internet or intranet access, a smart phone, a server, a server farm, an android device (or equivalent), a tablet, smartphones, and a personal digital assistant (PDA). Such a system may correspond to a computer system as described below with regard to FIG. 6.

Further, as discussed above, such a system may have corresponding software (e.g., user system software, sensor device software, controller software). The software may execute on the same or a separate device (e.g., a server, mainframe, desktop personal computer (PC), laptop, PDA, television, cable box, satellite box, kiosk, telephone, mobile phone, or other computing devices) and may be coupled by the communication network (e.g., Internet, Intranet, Extranet, LAN, WAN, or other network communication methods) and/or communication channels, with wire and/or wireless segments according to some example embodiments. The software of one system may be a part of, or operate separately but in conjunction with, the software of another system within the system 400.

Figure 6:
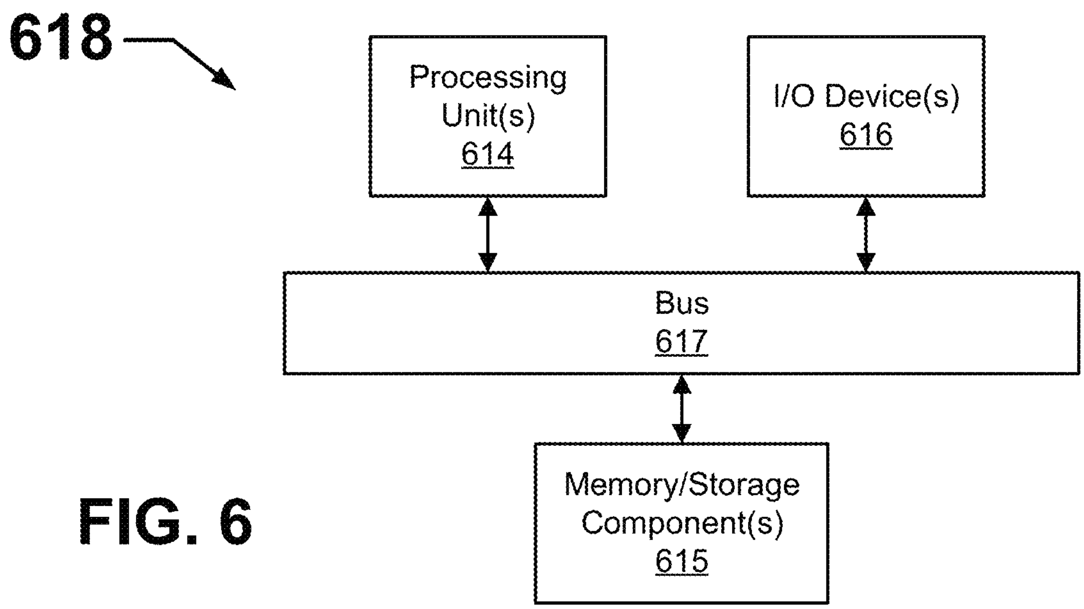
FIG. 6 shows a computing device in accordance with certain example embodiments.

FIG. 6 illustrates one embodiment of a computing device 618 that implements one or more of the various techniques described herein, and which is representative, in whole or in part, of the elements described herein pursuant to certain example embodiments. For example, a controller 404 (including components thereof, such as a control engine 506, a hardware processor 521, a storage repository 531, a power module 530, and a transceiver 524) may be considered a computing device 618 (also called a computer system 618 herein). Computing device 618 is one example of a computing device and is not intended to suggest any limitation as to scope of use or functionality of the computing device and/or its possible architectures. Neither should the computing device 618 be interpreted as having any dependency or requirement relating to any one or combination of components illustrated in the example computing device 618.

The computing device 618 includes one or more processors or processing units 614, one or more memory/storage components 615, one or more input/output (I/O) devices 616, and a bus 617 that allows the various components and devices to communicate with one another. The bus 617 represents one or more of any of several types of bus structures, including a memory bus or memory controller, a peripheral bus, an accelerated graphics port, and a processor or local bus using any of a variety of bus architectures. The bus 617 includes wired and/or wireless buses.

The memory/storage component 615 represents one or more computer storage media. The memory/storage component 615 includes volatile media (such as random access memory (RAM)) and/or nonvolatile media (such as read only memory (ROM), flash memory, optical disks, magnetic disks, and so forth). The memory/storage component 615 includes fixed media (e.g., RAM, ROM, a fixed hard drive, etc.) as well as removable media (e.g., a Flash memory drive, a removable hard drive, an optical disk, and so forth).

One or more I/O devices 616 allow a user 451 to enter commands and information to the computing device 618, and also allow information to be presented to the user 451 and/or other components or devices. Examples of input devices 616 include, but are not limited to, a keyboard, a cursor control device (e.g., a mouse), a microphone, a touchscreen, and a scanner. Examples of output devices include, but are not limited to, a display device (e.g., a monitor or projector), speakers, outputs to a lighting network (e.g., DMX card), a printer, and a network card.

Various techniques are described herein in the general context of software or program modules. Generally, software includes routines, programs, objects, components, data structures, and so forth that perform particular tasks or implement particular abstract data types. An implementation of these modules and techniques are stored on or transmitted across some form of computer readable media. Computer readable media is any available non-transitory medium or non-transitory media that is accessible by a computing device. By way of example, and not limitation, computer readable media includes "computer storage media".

"Computer storage media" and "computer readable medium" include volatile and non-volatile, removable and non-removable media implemented in any method or technology for storage of information such as computer readable instructions, data structures, program modules, or other data. Computer storage media include, but are not limited to, computer recordable media such as RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which is used to store the desired information and which is accessible by a computer.

The computer device 618 is connected to a network (not shown) (e.g., a LAN, a WAN such as the Internet, cloud, or any other similar type of network) via a network interface connection (not shown) according to some example embodiments. Those skilled in the art will appreciate that many different types of computer systems exist (e.g., desktop computer, a laptop computer, a personal media device, a mobile device, such as a cell phone or personal digital assistant, or any other computing system capable of executing computer readable instructions), and the aforementioned input and output means take other forms, now known or later developed, in other example embodiments. Generally speaking, the computer system 618 includes at least the minimal processing, input, and/or output means necessary to practice one or more embodiments.

Further, those skilled in the art will appreciate that one or more elements of the aforementioned computer device 618 is located at a remote location and connected to the other elements over a network in certain example embodiments. Further, one or more embodiments is implemented on a distributed system having one or more nodes, where each portion of the implementation (e.g., an injection gas insertion system 449, the analysis apparatus 470, the reaction module 475, the conveyance system 444) is located on a different node within the distributed system. In one or more embodiments, the node corresponds to a computer system. Alternatively, the node corresponds to a processor with associated physical memory in some example embodiments. The node alternatively corresponds to a processor with shared memory and/or resources in some example embodiments.

Figure 7:
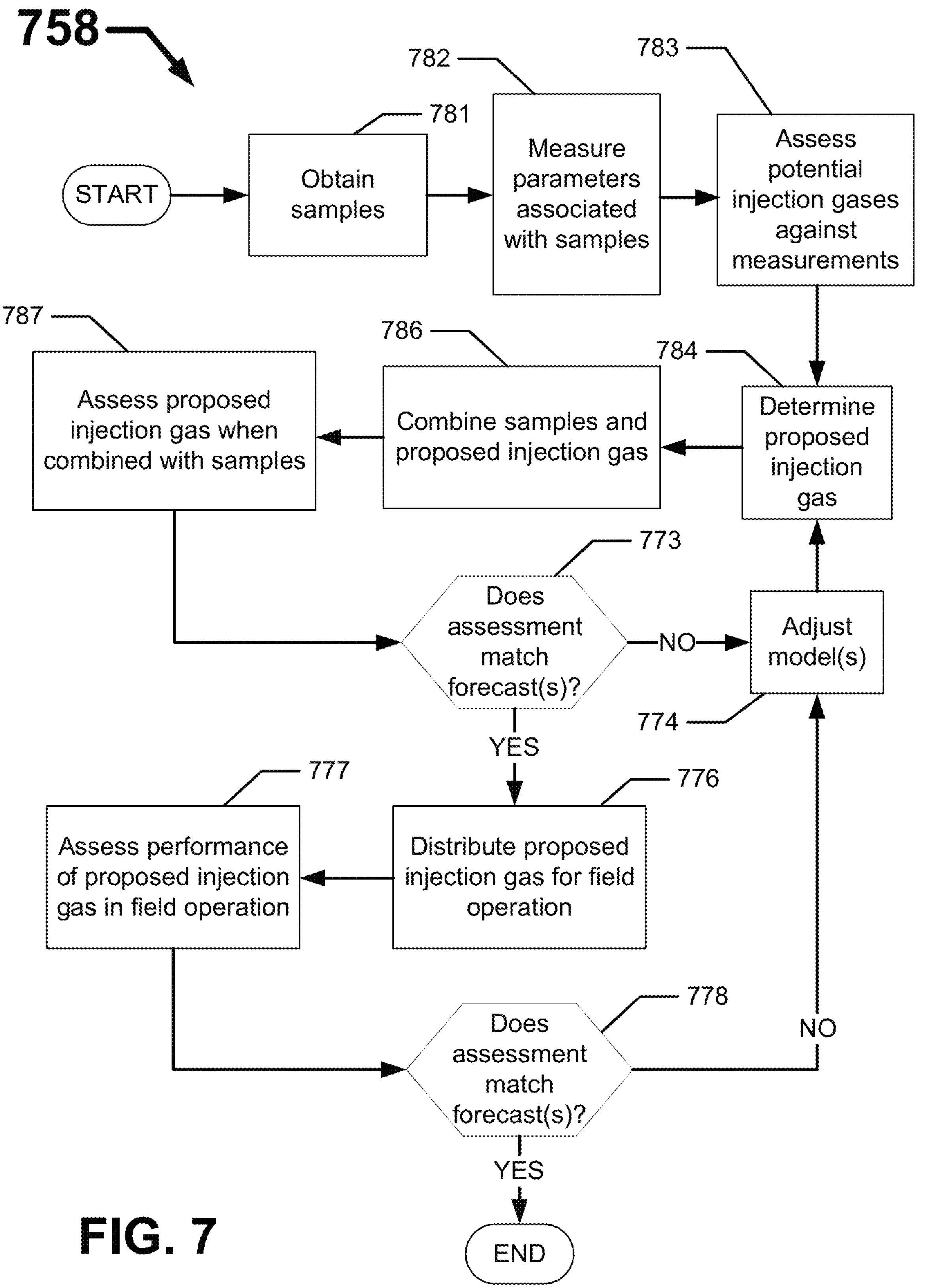
FIG. 7 shows a flowchart of a method for improving a field operation that includes a gas injection according to certain example embodiments.

FIG. 7 shows a flowchart 758 of a method for improving a field operation that includes a gas injection according to certain example embodiments. While the various steps in this flowchart 758 are presented sequentially, one of ordinary skill will appreciate that some or all of the steps may be executed in different orders, may be combined or omitted, and some or all of the steps may be executed in parallel. Further, in one or more of the example embodiments, one or more of the steps shown in this example method may be omitted, repeated, and/or performed in a different order. Some or all of the steps of the method of FIG. 7 may be performed off site (e.g., in a laboratory remote from a field operation). In addition, or in the alternative, some or all of the steps of the method of FIG. 7 may be performed on site (e.g., in the field, adjacent to a wellbore 120) where a field operation is being performed or planned.

In addition, a person of ordinary skill in the art will appreciate that additional steps not shown in FIG. 7 may be included in performing this method. Accordingly, the specific arrangement of steps should not be construed as limiting the scope. Further, a particular computing device, such as the computing device 618 discussed above with respect to FIG. 6, may be used to perform one or more of the steps for the methods shown in FIG. 7 in certain example embodiments. Any of the functions performed below by a controller 404 (an example of which is shown in FIG. 5) may involve the use of one or more protocols 532, one or more algorithms 533, and/or stored data 534 stored in a storage repository 531. In addition, or in the alternative, any of the functions in the method may be performed by a user (e.g., user 451). As discussed in the method, the proposed injection gas 445 may be a proposed single injection gas 445 or multiple proposed injection gases 445.

The method shown in FIG. 7 is merely an example that may be performed by using an example system described herein. In other words, systems for optimizing (e.g., improving) a field operation that includes a gas injection may perform other functions using other methods in addition to and/or aside from those shown in FIG. 7. Referring to FIGS. 1A through 7, the method shown in the flowchart 758 of FIG. 7 begins at the START step and proceeds to step 781, where samples 428 are obtained. As used herein, the term "obtaining" may include receiving, retrieving, accessing, generating, etc. or any other manner of obtaining the information or items (in this case, the identified samples 428). In the experiments, chemical additives (e.g., scale inhibitor, surfactant) may or may not be included in the fluid phase (especially, when we are looking into gas-water alternating injection) to investigate the impact of chemical additives under different injection gas compositions.

The samples 428 may be obtained from some or all of the conveyance system 444. The samples 428 may be obtained by the analysis apparatus 470 (or portion thereof). Some or all of the samples 428 may be obtained using a controller 404 (or an obtaining component thereof), which may include the controller 404 of FIG. 5 above, using one or more algorithms 533 and/or one or more protocols 532. In addition, or in the alternative, some or all of the samples 428 may be obtained from, or with the assistance of, a user 451, including an associated user system 455.

In step 782, one or more parameters associated with the samples 428 are determined (e.g., measured, calculated, modeled, plotted). The parameters may be measured by one or more sensor devices 460. In certain example embodiments, a parameter may be determined when the sample 428 is in a wellbore 420, in the analysis apparatus 470, or in the conveyance system 444 between the wellbore 420 and the analysis apparatus 470. A parameter measured by a sensor device 460 may be directly or indirectly associated with the sample 428. At least some of the parameters associated with the samples 428 may be fluid chemistry parameters. The measurements made by some or all of the sensor devices 460 may be at the direction of a controller 404 using one or more algorithms 533 and/or one or more protocols 532. In addition, or in the alternative, the measurements may be performed or directed by a user (e.g., user 451). The values of the measurements may be stored by the controller 404 in the storage repository 531.

Examples of measurements of the parameters associated with the samples 428 may include, but are not limited to, a composition of one or more samples 428, a temperature of one or more samples 428, and a pressure of one or more samples 428. Other examples of measurements of parameters associated with the samples 428 are discussed above with respect to FIGS. 4 and 5. The measurements may be obtained at one time, over a period of time, periodically, or on some other basis. The values of measurements may be from currently obtained samples 428. In addition, or in the alternative, the values of measurements may be historical (e.g., measurements obtained from samples 428 of a prior field operation of the wellbore 420 and/or the subterranean formation 110). In certain example embodiments, the parameters that are measured include fluid chemistry parameters and rock properties of the samples 428.

In certain example embodiments, a controller 404 may set and/or control the environment to which the samples 428 are exposed using one or more algorithms 533 and/or one or more protocols 532. For example, if a goal of the testing is to subject the samples 428 to conditions found in the subterranean formation 110, then the controller 404 may accordingly control factors such as the temperature and the pressure applied to the samples 428 when the measurements of the parameters are taken by the sensor devices 460.

Examples of parameters associated with a sample 428 that are determined (e.g., measured, calculated, modeled) may include, but are not limited to, the composition or chemistry of the produced water 147, the amount (concentration) of each part of the composition, the amount and type of TDSs in the produced water 147, the state (e.g., liquid, solid) of each part of the composition, temperature, pH, viscosity, chemistry of in situ water at the wellbore 420, minerology at the wellbore 420, temperature at the wellbore 420, pressure at the wellbore 420, scaling/solid formation potential, carbon dioxide and/or hydrogen sulfide content in gas produced from the wellbore 420, carbon dioxide and/or hydrogen sulfide content in gas produced from an adjacent wellbore 420 to the wellbore 420, and carbon dioxide and/or hydrogen sulfide content in gas produced from fields unrelated to a field that includes the wellbore 420 and the adjacent wellbore 420.

In step 783, multiple potential injection gases 445 are assessed against the values of the measurements of the parameters associated with the samples 428. Some or all of the process of assessing the potential injection gases 445 against the values of the measurements of the parameters associated with the samples 428 may be controlled by the analysis module 550 of a controller 404 (or an evaluation component thereof) using one or more protocols 532, one or more algorithms 533 (e.g., models), values of measurements of one or more sensor devices 460, input from a user 451 (which may include an associated user system 455), and/or any other source of information within the system 400. In addition, or in the alternative, some or all of the process of assessing the potential injection gases 445 against the values of the measurements of the parameters associated with the samples 428 may be controlled by a user 451. The values of measurements may include values of raw measurements made by sensor devices 460, values of adjusted measurements made by sensor devices 460, outputs of models using values of measurements made by sensor devices 460 as inputs, some other information associated with measurements made by sensor devices 460, or any suitable combination thereof.

In some cases, assessing the potential injection gases 445 against the values of measurements of the parameters associated with the samples 428 may include developing strategies and forecasts that may be used in one or more steps below (e.g., step 784). Chemistry calculations based on the evaluated results of this step 783 may be performed. In addition to modeling, lab testing and/or other evaluation methods may be used to assess the potential impacts of injection gases 445 against the values of the measurements of the parameters associated with the samples 428. In certain example embodiments, each of the potential injection gases 445 includes an acidic component (e.g., $CO_2$, $H_2S$).

Assessing the potential injection gases 445 against the values of the measurements of the parameters associated with the samples 428 may be performed continuously over an extended period of time or on a discrete basis. The assessment may involve the use of historical data, other present data, and/or forecasts. The assessment may involve data for the particular wellbore 420 from which a sample 428 is extracted, for other adjacent wells that are part of the same pad, upcoming wells in a targeted formation, and/or for other wells in other locations. In certain example embodiments, in addition to the values of the measurements of the parameters associated with the samples 428 being used in the assessment, the values of the measurements of other parameters that may have been tested in step 782 may be used in the assessment. In any case, the assessment may be in terms of chemistry, geology, economics, some other variable, or any suitable combination thereof.

In some cases, two or more of the potential injection gases 445 may be assessed simultaneously. The reaction module 475 in which a potential injection gas 445 is assessed may be or include a lab (e.g., a traditional laboratory) and/or may include chemistry modeling or calculations with a software tool. In some cases, assessing the potential injection gases against the values of the measurements of parameters associated with the samples may include modeling/measuring a pH of in situ water, modeling/measuring rock-water interaction, determining an impact of the acidic component of a potential injection gas 445 on scale and asphaltene deposition in the wellbore 420 with gas injection, determining the impact of the acidic component of a potential injection gas 445 on scale and asphaltene deposition on adjacent wellbores 420, and/or determining an impact of the acidic component of a potential injection gas 445 and water chemistry on at least one of a group consisting of oil recovery, rock fracture surfaces, and porous media. In some cases, assessing the potential injection gases 445 against the values of the measurements of the parameters associated with the samples 428 may include other factors, including but not limited to adjusting the chemistry of the water, adjusting the injection pressure, and selecting another wellbore 420 and/or formation for gas injection deployment.

In step 784, a proposed injection gas 445 is determined. The proposed injection gas 445 may be among multiple injection gases 445 available for a field operation. The proposed injection gas 445 is used in the field operation. Some or all of the process of determining a proposed injection gas 445 may be controlled by the analysis module 550 of a controller 404 (or a selection component thereof) using one or more protocols 532, one or more algorithms 533 (e.g., models), input from a user 451 (which may include an associated user system 455), and/or any other source within the system 400. In addition, or in the alternative, some or all of the process of determining a proposed injection gas 445 may be controlled by a user 451. Determining the proposed injection gas 445 may be based on expected results of using that proposed injection gas 445 in combination with the samples 428 in a subterranean field operation on a wellbore 420.

Determining a proposed injection gas 445 may include determining a composition of the injection gas 445 and/or determining a concentration or amount of the injection gas 445. The injection gas 445 may be selected based on the results evaluated in step 783 or in step 774 (discussed below). If this step 784 represents a repeated step in the method, then determining a proposed injection gas 445 may include determining a new proposed injection gas 445 in place of a previously-selected proposed injection gas 445 and/or selecting a different concentration or amount of the proposed injection gas 445 compared to a concentration or amount previously selected for that proposed injection gas 445. In some cases, rather than determining a single proposed injection gas 445, multiple proposed injection gases 445 may be determined in this step 784.

Determining the proposed injection gas 445 may be done by generating one or more of a number of forecasts. Such forecasts may be with respect to in terms of chemistry, the impact on well performance/production risks, the impact on field operations/product value/operational cost, overall economics, some other factor, or any suitable combination thereof. As some non-exclusive examples, the determination may be made with respect to the economic impacts of hydrocarbon recovery, improved performance of SWD wells, acidic gas-induced corrosion issues and/or casing failures, downtime and cost of fixing fluid compatibility related well failures (e.g., due to scale depositions 213), and the impact of the economic assessment for future refracturing operations of the wellbore 420.

In some cases, the proposed injection gas 445 may be displayed in a visual representation to a user 451 using a display or other type of user interface (e.g., the user system 455). In such cases, a controller 404 may be responsible for displaying the proposed injection gas 445 using one or more protocols 532, one or more algorithms 533 (e.g., models), input from a user 451 (which may include an associated user system 455), and/or any other source within the system 400.

In step 786, the proposed injection gas 445 and the samples 428 are combined. In certain example embodiments, the proposed injection gas 445 and the samples 428 are combined in the reaction module 475 and/or in the conveyance system 444 feeding the proposed injection gas 445 and/or the samples 428 to the reaction module 475. Chemical additives such as scale inhibitor and surfactant may be included in the reaction. Some or all of the process of combining the proposed injection gas 445 and the samples 428 may be controlled by the analysis module 550 of a controller 404 (or a combining component thereof) using one or more protocols 532, one or more algorithms 533 (e.g., models), input from a user 451 (which may include an associated user system 455), and/or any other source within the system 400. In addition, or in the alternative, some or all of the process of combining the proposed injection gas 445 and the samples 428 may be controlled by a user 451.

Each sample 428 may be removed from a wellbore 420 using part of the conveyance system 444. The proposed injection gas 445 may be removed from one or more injection gas sources 448 using one or more injection gas insertion systems 449 and another part of the conveyance system 444. The proposed injection gas 445 and the samples 428 may be combined using equipment (e.g., a mixer, a blower, a centrifuge) of the reaction module 475. When multiple proposed injection gases 445 are selected in step 784, all of the proposed injection gases 445 may be combined with all of the samples 428 at once. Alternatively, when multiple proposed injection gases 445 are selected in step 784, each proposed injection gas 445 may be combined with some or all of the samples 428 independently of each other.

In step 787, the proposed injection gas 445 is assessed after being combined with the samples 428. Some or all of the process of assessing the proposed injection gas 445 after being combined with the samples 428 may be controlled by the analysis module 550 of a controller 404 (or a combining component thereof) using one or more protocols 532, one or more algorithms 533 (e.g., models), input from a user 451 (which may include an associated user system 455), and/or any other source within the system 400. In addition, or in the alternative, some or all of the process of assessing the proposed injection gas 445 after being combined with the samples 428 may be controlled by a user 451.

The proposed injection gas 445 may be assessed in the reaction module 475. Assessing the proposed injection gas 445 may be based on the values of raw measurements made by sensor devices 460, the values of adjusted measurements made by sensor devices 460, outputs of models using the values of measurements made by sensor devices 460 as inputs, some other information associated with the values of measurements made by sensor devices 460, or any suitable combination thereof. The assessment may be made continuously over an extended period of time or on a discrete basis. The assessment may be conducted using historical data, other present data, and/or forecasts. The assessment may be evaluated against data for the particular wellbore 420 from which the samples 428 are extracted, for other adjacent wellbores 420 that are part of the same pad, and/or for other wells (e.g., a SWD well) in other locations.

In certain example embodiments, in addition to assessing the proposed injection gas 445, other elements and/or aspects of the wellbore 420 and/or other wells may also be evaluated in this step 787. In any case, the assessment of the proposed injection gas 445 may be in terms of chemistry, economics (e.g., considering the cost of the proposed injection gas 445, increased revenue due to improved production/reduced downtime for a field operation, etc.), some other factor, or any suitable combination thereof. Assessing the proposed injection gas 445 may be based on the values of raw measurements made by sensor devices 460, the values of adjusted measurements made by sensor devices 460, outputs of models using the values of measurements made by sensor devices 460 as inputs, some other information associated with the values of measurements made by sensor devices 460, or any suitable combination thereof.

In step 773, a determination is made as to whether the assessment of the proposed injection gas 445 when combined with the samples 428 matches the forecast that was used to select the proposed injection gas 445 in step 784. The assessment may be with respect to predicted characteristics of the proposed injection gas 445, one or more of the samples 428, a byproduct of a combination of the proposed injection gas 445 and one or more of the samples 428, the wellbore 420, another well, or any suitable combination thereof. The forecasts may be in terms of chemistry, geology, economics, some other factor, or any suitable combination thereof.

Some or all of the determination may be made by the analysis module 550 of a controller 404 (or a determining component thereof) using one or more protocols 532, one or more algorithms 533 (e.g., models), input from a user 451 (which may include an associated user system 455), and/or any other source within the system 400. In addition, or in the alternative, some or all of the determination may be made may be controlled by a user 451. If the assessment matches the forecast, then the process proceeds to step 776. If the assessment does not match the forecast, then the process proceeds to step 774.

In step 774, one or more of the models (forms of algorithms 533) is adjusted. One or more of the models may be adjusted using the actual data (e.g., the values of measurements by sensor devices 460) and/or differences between actual data and forecasts. For example, a model that calculates and determines the concentration of a proposed injection gas 445 may be adjusted. As another example, a model that determines the chemical composition of a proposed injection gas 445 may be updated. As yet another example, a model that calculates and determines the one or more states (e.g., gas, liquid, solid), including any proportions thereof, of a proposed injection gas 445 may be adjusted. Some or all of the adjustments to one or more of the models may be made by a controller 404 (or an adjusting component thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the adjustments to one or more of the models may be made by a user 451. When step 774 is complete, the process may revert to step 784.

In step 776, the proposed injection gas 445 is distributed to one or more field operations. The proposed injection gas 445 may be distributed to one or more field operations using parts of the conveyance system 444. A field operation may be directed to the same wellbore 420 from which the samples 428 are extracted, a different wellbore 420 that shares a pad with the wellbore 420 from which the samples 428 are extracted, or some other wellbore.

Some or all of the process of distributing the proposed injection gas 445 may be controlled by a controller 404 (or a collecting component thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the process of distributing the proposed injection gas 445 may be controlled by a user 451. The distribution process may be controlled using measurements from one or more sensor devices 460.

In some cases, prior to distributing the proposed injection gas 445, the proposed injection gas 445 may be prepared for distribution. Preparing the proposed injection gas 445 may be considered part of the distribution process. Actions involved in preparing the proposed injection gas 445 may include, but are not limited to, ordering the proposed injection gas 445 from a vendor, mixing chemical components to generate the proposed injection gas 445, mixing multiple injection gases 445 to generate the proposed injection gas 445, controlling the temperature, pressure, and/or other variables of the proposed injection gas 445. "Using" the proposed injection gas 445 may include injecting the proposed injection gas 445 in a field operation comprising the gas injection.

In step 777, the performance of the proposed injection gas 445 is assessed in the field operation. Some or all of the process of assessing the proposed injection gas 445 in the field operation may be controlled by a controller 404 (or an assessment component thereof) using one or more protocols 532, one or more algorithms 533 (e.g., models), measurements of one or more sensor devices 460, input from a user 451 (which may include an associated user system 455), and/or any other source of information within the system 400. In addition, or in the alternative, some or all of the process of assessing the proposed injection gas 445 in the field operation may be controlled by a user 451. Assessing the proposed injection gas 445 in the field operation may be based on the values of raw measurements made by sensor devices 460, the values of adjusted measurements made by sensor devices 460, outputs of models using the values of measurements made by sensor devices 460 as inputs, some other information associated with the values of measurements made by sensor devices 460, or any suitable combination thereof.

The assessment may be performed continuously over an extended period of time or on a discrete basis. The assessment may be performed using historical data, other present data, and/or forecasts. The assessment may be performed using data for the particular wellbore 420 on which the field operation is directed, for other adjacent wells that are part of the same pad, for upcoming/future developments, and/or for other wells (e.g., a SWD well) in other locations. In certain example embodiments, in addition to assessing the proposed injection gas 445, other elements (e.g., water chemistry, chemical additives), operation conditions (e.g., temperature, pressure), and/or aspects of the wellbore 420 and/or other wells may also be evaluated in this step 777. For example, one or more samples 428 extracted from the wellbore 420 during and/or after the field operation may be assessed in this step 777. As another example, one or more byproducts generated during the field operation in the wellbore 420 may be assessed in this step 777. In any case, the evaluation may be in terms of chemistry, geology, the impact on well performance, the impact on the field operation, overall economics, some other factor, or any suitable combination thereof.

As a specific example, assessing the performance of the proposed injection gas 445 may be based on, using the values of measurements made by one or more sensor devices 460, scale accumulation 213, presence of corrosion, asphaltene analysis, the production profile of the wellbore 420 with the proposed injection gas 445, the production profile of an adjacent wellbore 420, injectivity of the wellbore 420, the pressure of the wellbore 420 with the proposed injection gas 445, the chemistry of the produced water 147 from the wellbore 420, the composition of the hydrocarbons (and/or other subterranean resources 111) produced from the wellbore 420, the impact of gas-water-rock interaction and inter-well water migration based on water chemistry data, production data of the wellbore 420, other surveillance data (e.g., pressure) of the wellbore 420, mineral trapping of $CO_2$, and/or mass balance.

In step 778, a determination is made as to whether the assessment in step 777 matches one or more of the forecasts that were used to select the proposed injection gas 445 in step 784. The assessment may be with respect to predicted characteristics of the proposed injection gas 445, predicted impact on oil recovery, predicted characteristics of one or more of the samples 428, a byproduct of a combination of the proposed injection gas 445 and one or more of the samples 428, predicted characteristics of the wellbore 420, predicted characteristics of another well, predicted results of the field operation, some other variable, or any suitable combination thereof. The forecasts may be in terms of chemistry, geology, economics, some other factor, or any suitable combination thereof.

Some or all of the determination may be made by the analysis module 550 of a controller 404 (or a determining component thereof) using one or more protocols 532, one or more algorithms 533 (e.g., models), input from a user 451 (which may include an associated user system 455), and/or any other source within the system 400. In addition, or in the alternative, some or all of the determination may be made may be controlled by a user 451. If the assessment of the actual results matches the forecast, then the process proceeds to the END step. If the assessment of the actual results does not match the forecast, then the process reverts to step 774, where adjusting a model used for assessing the potential injection gases 445 against the values of the measurements of the parameters associated with the samples 428 may be based on the actual results (i.e., the data collected while the proposed injection gas 445 is used during the subterranean operation performed on the wellbore 420).

The amount of time that the evaluations conducted in this method may be extended (e.g., one month, two months, three months) to simulate a different stage (e.g., a shut-in stage, which occurs after a fracturing stage) of a field operation. Further, during this subsequent stage in a field operation at the subsurface, the contents of the proposed injection gas 445 in the near-wellbore formation may change. In such cases, the contents and/or concentrations of the proposed injection gas 445 may be changed during the extended testing period to simulate subsurface conditions as much as possible.

In addition to the duration of the evaluations performed using this method and adjusting the contents/concentrations of the proposed injection gas 445, other aspects of the evaluations may additionally or alternatively be controlled. For example, the testing environment may be controlled in terms of the pressure and/or temperature that is asserted on the fluid (which includes the proposed injection gas 445) used at the subsurface. In addition, or in the alternative, the flow rate and injection pressure of the proposed injection gas 445 flowing through the rock matrices at the subsurface may be simulated during the evaluations. In such cases, the values of the temperature, the pressure, and/or the flow rate may differ at different points of the duration of the testing, in some cases in an attempt to simulate the various stages (e.g., hydraulic fracturing, shut-in) of a subterranean field operation.

In certain example embodiments, multiple tests are performed simultaneously (in parallel with each other). In such cases, each of the multiple tests may be distinguished from the other simultaneous tests by varying one or more of a number of factors, including but not limited to the duration of the test, the composition of the proposed injection gas 445, the type and/or amount of additives used to interact with the proposed injection gas 445, and the proportions (amounts or concentrations) of each of the proposed injection gas 445.

Figure 8:
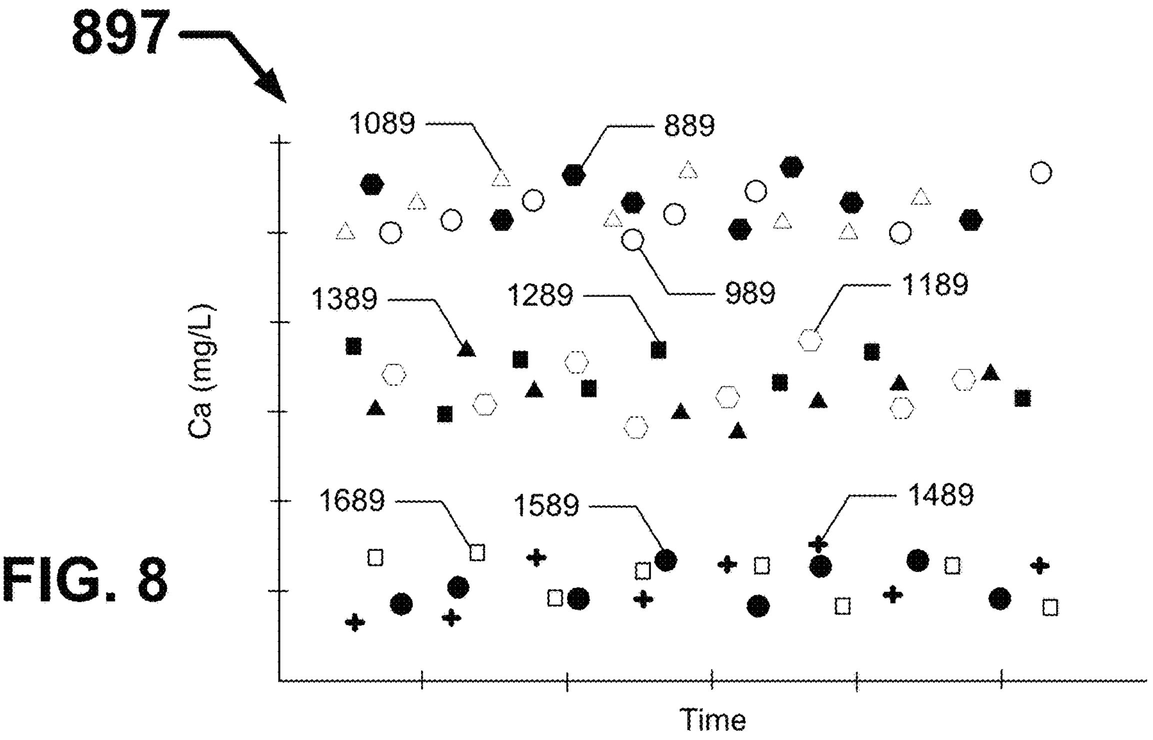

FIGS. 8 through 13 show graphs of a time lapse fluid chemistry study used to optimize (e.g., improve) a field operation using a gas injection according to certain example embodiments. Referring to FIGS. 1A through 13, the graph 897 of FIG. 8 plots the values of measurements for calcium (Ca) for multiple samples (e.g., sample 428) taken from multiple wellbores over time. In the graph 897, the horizontal axis is in terms of time (e.g., days, weeks, months), and the vertical axis is in terms of Ca in mg/L.

In the graph 897 of FIG. 8, there are 8 values of measurements 889 for Ca, shown as solid hexagons in the graph 897, taken from 8 samples from one wellbore. There are 8 values of measurements 989 for Ca, shown as outlined circles in the graph 897, taken from 8 samples from a second wellbore. There are 8 values of measurements 1089 for Ca, shown as outlined circles in the graph 897, taken from 8 samples from a third wellbore. There are 8 values of measurements 1189 for Ca, shown as outlined hexagons in the graph 897, taken from 8 samples from a fourth wellbore.

There are 8 values of measurements 1289 for Ca, shown as solid squares in the graph 897, taken from 8 samples from a fifth wellbore. There are 8 values of measurements 1389 for Ca, shown as solid triangles in the graph 897, taken from 8 samples from a sixth wellbore. There are 8 values of measurements 1489 for Ca, shown as "+"s in the graph 897, taken from 8 samples from a seventh wellbore. There are 8 values of measurements 1589 for Ca, shown as solid circles in the graph 897, taken from 8 samples from an eighth wellbore. There are 8 values of measurements 1689 for Ca, shown as outlined squares in the graph 897, taken from 8 samples from a ninth wellbore.

In an effort to find subsurface water chemistry heterogeneity, as a result of the data collected, the wells may be divided into 3 groups based on the calibrated water chemistry surveillance data prior to gas injection. Specifically, the wellbores associated with measurements 889, measurements 989, and measurements 1089 may be categorized in one group. The wellbores associated with measurements 1189, measurements 1289, and measurements 1389 may be categorized in a second group. The wellbores associated with measurements 1489, measurements 1589, and measurements 1689 may be categorized in a third group.

Figure 9:
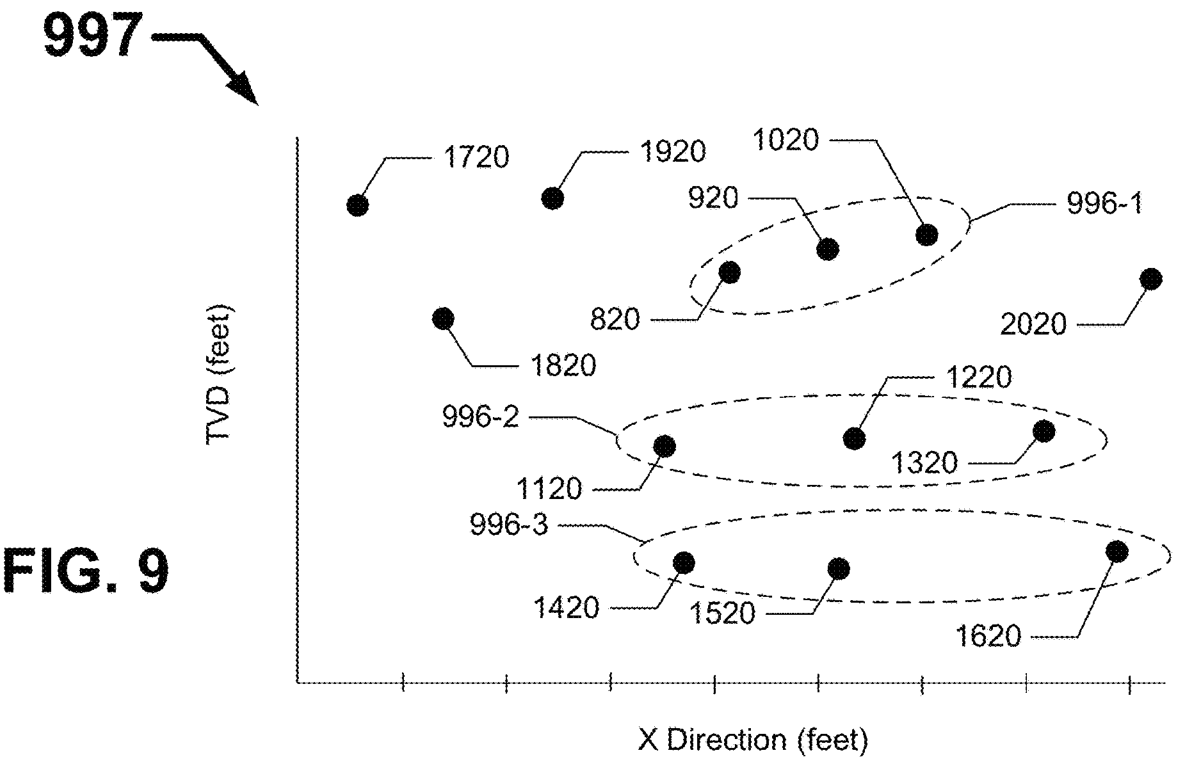

This grouping of the wellbores of FIG. 8 is also shown in the graph 997 of FIG. 9, which plots the wellbores from which the samples used in the graph 897 of FIG. 8 are taken in terms of total vertical depth (TVD) in feet along the vertical axis and displacement in the X-direction in feet along the horizontal axis. In the graph 997, group 996-1 includes wellbore 820 (from which the values of the measurements 889 in the graph 897 of FIG. 8 are taken), wellbore 920 (from which the values of the measurements 989 in the graph 897 of FIG. 8 are taken), and wellbore 1020 (from which the values of the measurements 1089 in the graph 897 of FIG. 8 are taken).

Group 996-2 includes wellbore 1120 (from which the values of the measurements 1189 in the graph 897 of FIG. 8 are taken), wellbore 1220 (from which the values of the measurements 1289 in the graph 897 of FIG. 8 are taken), and wellbore 1320 (from which the values of the measurements 1389 in the graph 897 of FIG. 8 are taken). Group 996-3 includes wellbore 1420 (from which the values of the measurements 1489 in the graph 897 of FIG. 8 are taken), wellbore 1520 (from which the values of the measurements 1589 in the graph 897 of FIG. 8 are taken), and wellbore 1620 (from which the values of the measurements 1689 in the graph 897 of FIG. 8 are taken).

The water chemistry data captured in the graph 897 of FIG. 8 indicates that the wellbores in group 996-3 may be significantly less connected to the wellbores in group 996-1 compared to the wellbores in group 996-2. This is consistent with the observation that more wellbores are impacted when gas injection occurs at wellbore 1220 compared to when gas injection occurs at wellbore 1420 in a field case study.

Figure 10:
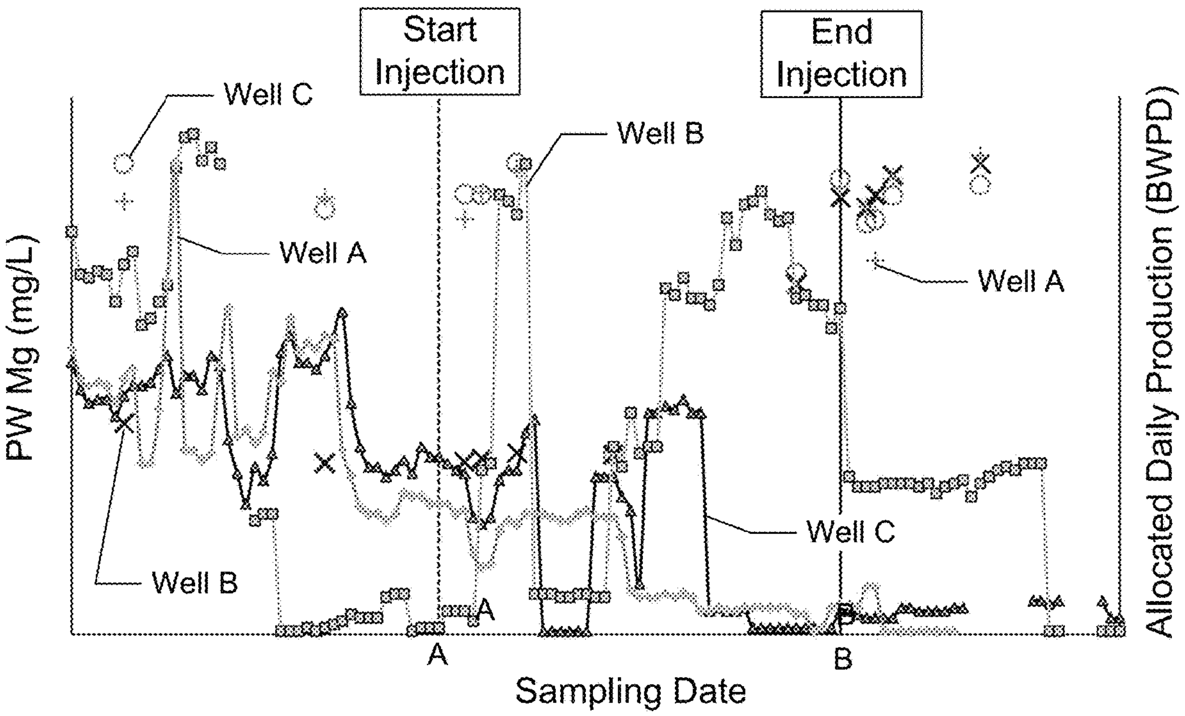

The graph 1097 of FIG. 10 shows plots of data associated with three wellbores. Specifically, the graph 1097 of FIG. 10 plots the values of measurements for magnesium (Mg) for multiple samples (e.g., sample 428) taken from wellbore A, wellbore B, and wellbore C over time. In the graph 1097, the horizontal axis is in terms of time (e.g., days, weeks, months), the vertical axis on the left is in terms of produced water (PW) Mg in mg/L, and the vertical axis on the right is in terms of daily production in barrels of water per day (BWPD). During the time frame captured in the graph 1097, a gas injection operation is being executed in another wellbore D adjacent to wellbore A, wellbore B, and wellbore C between time A and time B. The time lapse produced water chemistry data and produced water rate profile of the graph 1097 suggests a likely occurrence of inter-well water communication (e.g., suspected water migration) due to gas injection from wellbore B and wellbore A to wellbore C due to injection at wellbore D. The shapes in graph 1097 correspond to the vertical axis on the left (Mg in mg/L), and the lines in the graph 1097 correspond to the vertical axis on the right (daily production of water in BWPD).

Figure 11:
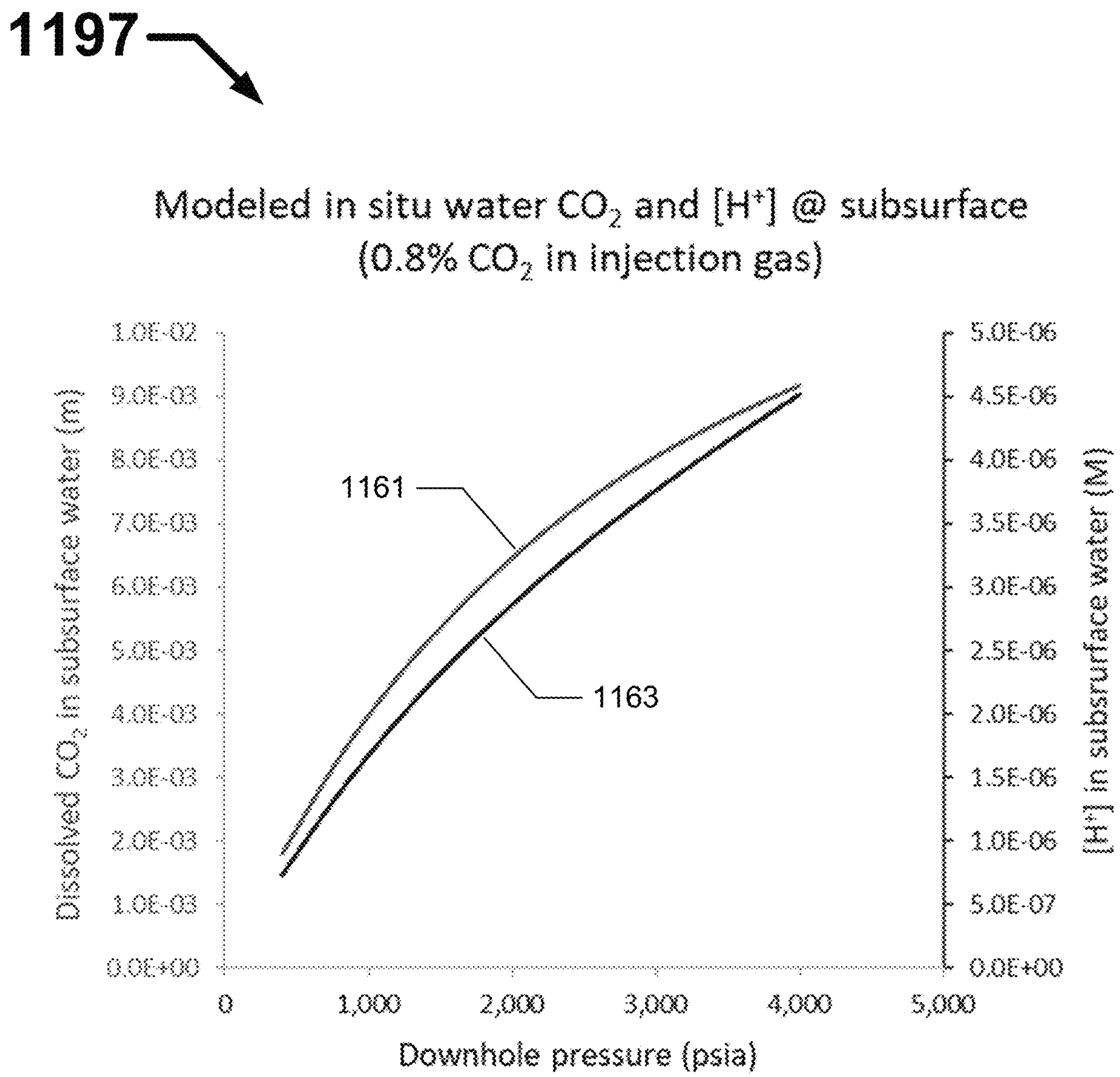

The graphs of FIGS. 11 through 13 show results when gas injection is being implemented on wellbore 1220 of FIGS. 8 through 10. Specifically, the graphs of FIGS. 11 through 13 show fluid chemistry modeling results and measured time-lapse produced water chemistry surveillance data for the gas injection (with $CO_2$ concentration of 0.8% in injection gas) at wellbore 1220. The graph 1197 of FIG. 11 shows plots of modelled dissolved $CO_2$ and $H^+$ concentrations in downhole aqueous phase (e.g., formation water 147) in the near wellbore 1220 region with 0.8% of $CO_2$ used as an injection gas (e.g., injection gas 445). In the graph 1197, the horizontal axis is in terms of downhole pressure (in psia) in/near the wellbore 1220, the vertical axis on the left is in terms of dissolved $CO_2$ (in m (moles per kg)) in the downhole aqueous phase, and the vertical axis on the right is in terms of $H^+$ (in M (moles per liter)) in the downhole aqueous phase. Plot 1161 shows the modeled dissolved $CO_2$ in the downhole aqueous phase over a range of downhole pressure from approximately 800 psia to approximately 4000 psia. Plot 1163 shows the modeled $H^+$ concentration in the downhole aqueous phase from approximately 800 psia to approximately 4000 psia.

The graph 1297 of FIG. 12 plots the values of measurements 1264 for dissolved $CO_2$ in the produced water (PW) from wellbore 1220 over time. In the graph 1297, the horizontal axis is in terms of sampling time (e.g., months), and the vertical axis is in terms of dissolved $CO_2$ in mg/L in the wellhead produced water from wellbore 1220. Up until time A, which represents when the first cycle of gas injection begins, there are 11 measurements 1264 where the dissolved $CO_2$ is no greater than 600 mg/L. Between times A and B, the first cycle of gas injection occurs at wellbore 1220, and no measurements 1264 are taken during this time. After time B, there are 6 measurements 1264 taken within a short time of each other. The values of these measurements 1264 of dissolved $CO_2$ range from 400 mg/L to 1200 mg/L, showing the effect of the gas injection on dissolved $CO_2$ in produced water from the wellbore 1220.

The graph 1397 of FIG. 13 plots the values of measurements 1266 for Mg and the values of measurements 1267 for a ratio of Ca to Mg in the produced water (PW) from wellbore 1220 over time. In the graph 1397, the horizontal axis is in terms of time (e.g., months), the vertical axis on the left is in terms of Mg in mg/L in the produced water, and the vertical axis on the right is in terms of the ratio of Ca to Mg (unitless, mg/L to mg/L) in the produced water from wellbore 1220. In the time covered in the graph 1397, there are 9 cycles in which an injection gas is pumped into the wellbore 1220 or other nearby wells. The first injection cycle starts at time A, and the last injection cycle ends at time B. Prior to time A, there are 10 measurements 1266 where the Mg is between approximately 300 mg/L and 500 mg/L, and there are 10 measurements 1267 where the ratio of Ca to Mg is between approximately 6.5 and 8.0.

After the first injection cycle is complete and before the second injection cycle begins, there are 6 measurements 1266 where the Mg is between approximately 500 mg/L and 560 mg/L, and there are 6 measurements 1267 where the ratio of Ca to Mg is between approximately 6.1 and 6.4.

Between the end of the seventh injection cycle and the start of the final (ninth) injection cycle, there are 12 measurements 1266 where the Mg is between approximately 540 mg/L and 700 mg/L, and there are 12 measurements 1267 where the ratio of Ca to Mg is between approximately 5.4 and 6.3.

Figure 14:
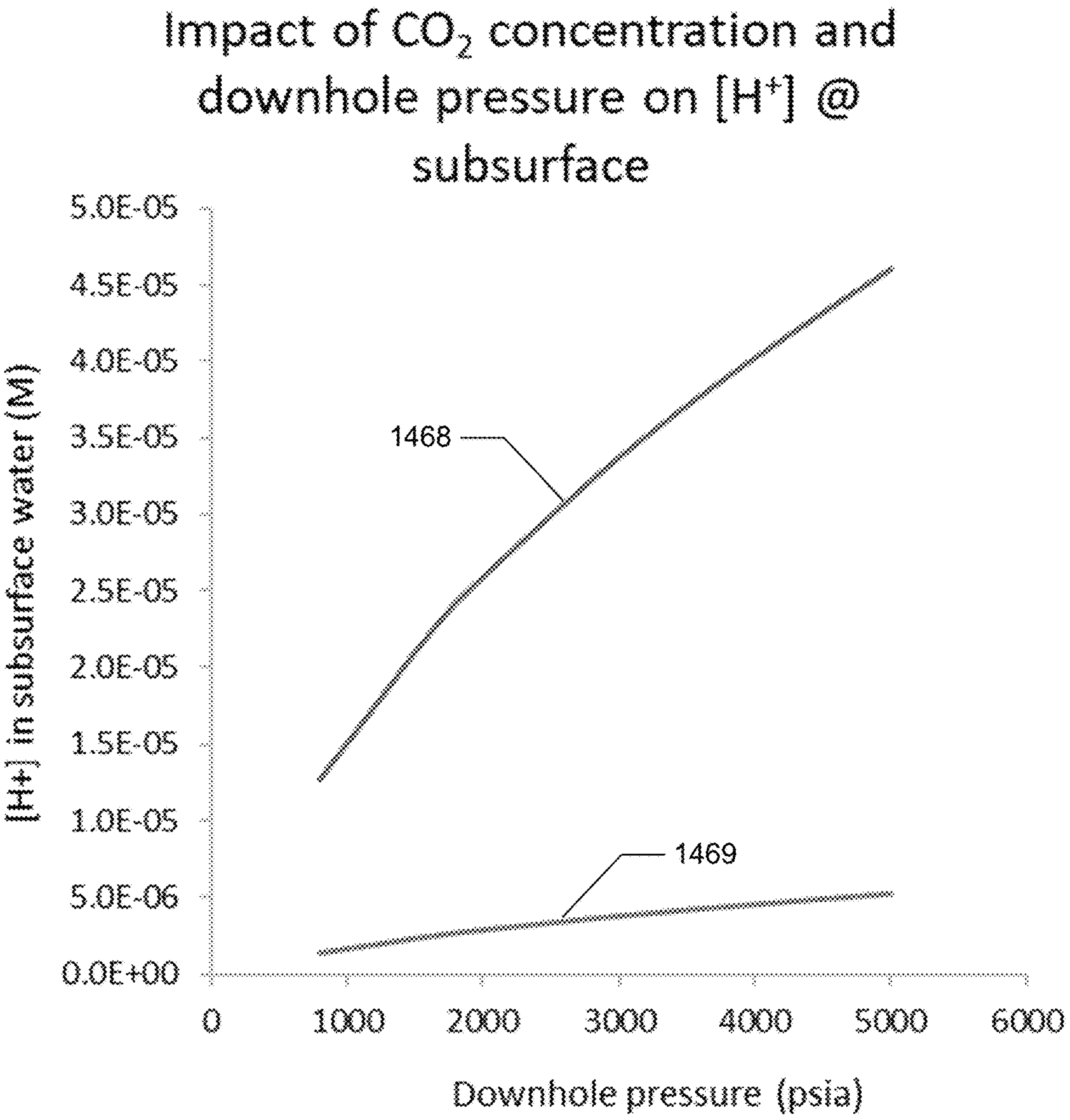
FIGS. 14 through 17 show graphs based on fluid chemistry modeling results according to certain example embodiments.
Figure 15:
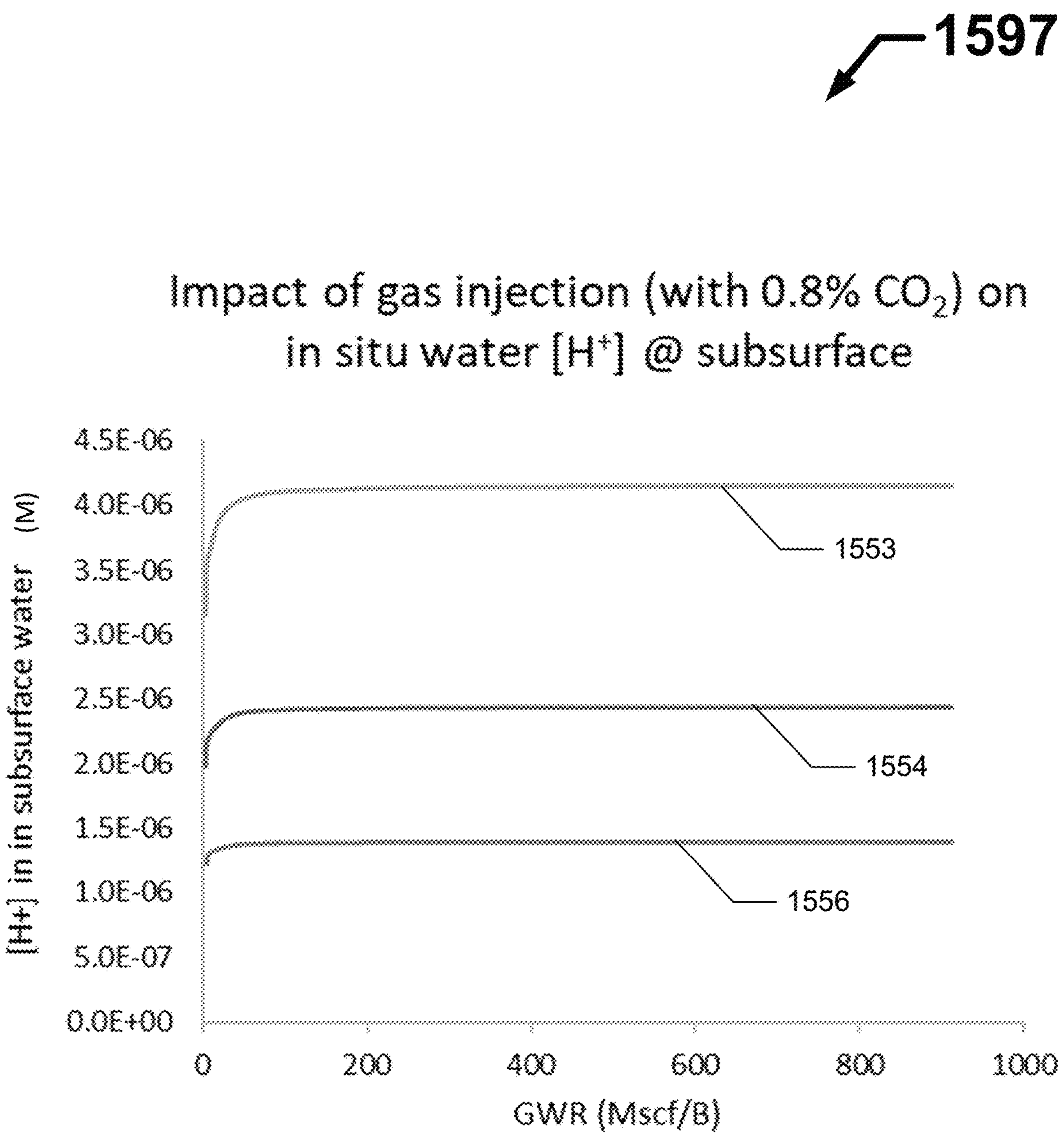

FIGS. 14 through 17 show graphs based on fluid chemistry modeling results according to certain example embodiments. Referring to FIGS. 1A through 17, the graphs of FIGS. 14 and 15 show fluid chemistry modeling results that suggest in situ water acidity/reactivity with rock increases with $CO_2$ concentration and downhole pressure. The graph 1497 of FIG. 14 shows plots of an injection gas (e.g., injection gas 445) with acidic content in the form of $CO_2$ to show its impact on in situ water pH at downhole when thermodynamic equilibrium is reached. In the graph 1497, the horizontal axis is in terms of pressure (in psia) in a wellbore (e.g., wellbore 420), and the vertical axis is in terms of modeled $H^+$ concentration (in M (moles per liter)) in the in situ water at downhole/near wellbore region. Plot 1468 shows the injection gas with 7.5% $CO_2$ over a range of downhole pressure from approximately 800 psia to approximately 5000 psia. In this case, the modeled $H^+$ concentration ranges from $1.2\times10^{-5}$ M to $4.5\times10^{-5}$ M. Plot 1469 shows the modeled results for the injection gas with 0.8% $CO_2$ over a range of downhole pressure from approximately 800 psia to approximately 5000 psia. In this case, the modeled $H^+$ concentration does not exceed $5.0\times10^{-6}$ M.

The graph 1597 of FIG. 15 shows plots of modeled results regarding an injection gas (e.g., injection gas 445) with acidic content in the form of 0.8% $CO_2$ to show its impact on $H^+$ concentration in water at downhole/in the near wellbore region at different pressures. In the graph 1597, the horizontal axis is in terms of average gas to water ratio (in Mscf/B) in a wellbore (e.g., wellbore 420), and the vertical axis is in terms of modeled $H^+$ concentration (in M) in water. Plot 1553 shows modeled results under downhole pressure of 3500 psia. In this case, the $H^+$ concentration is approximately $4.0\times10^{-6}$ M. Plot 1554 shows modeled results under downhole pressure of 1600 psia. In this case, the $H^+$ concentration is approximately $2.3\times10^{-6}$ M. Plot 1556 shows modeled results under downhole pressure of 800 psia. In this case, the $H^+$ concentration is approximately $1.3\times10^{-6}$ M.

Figure 16:
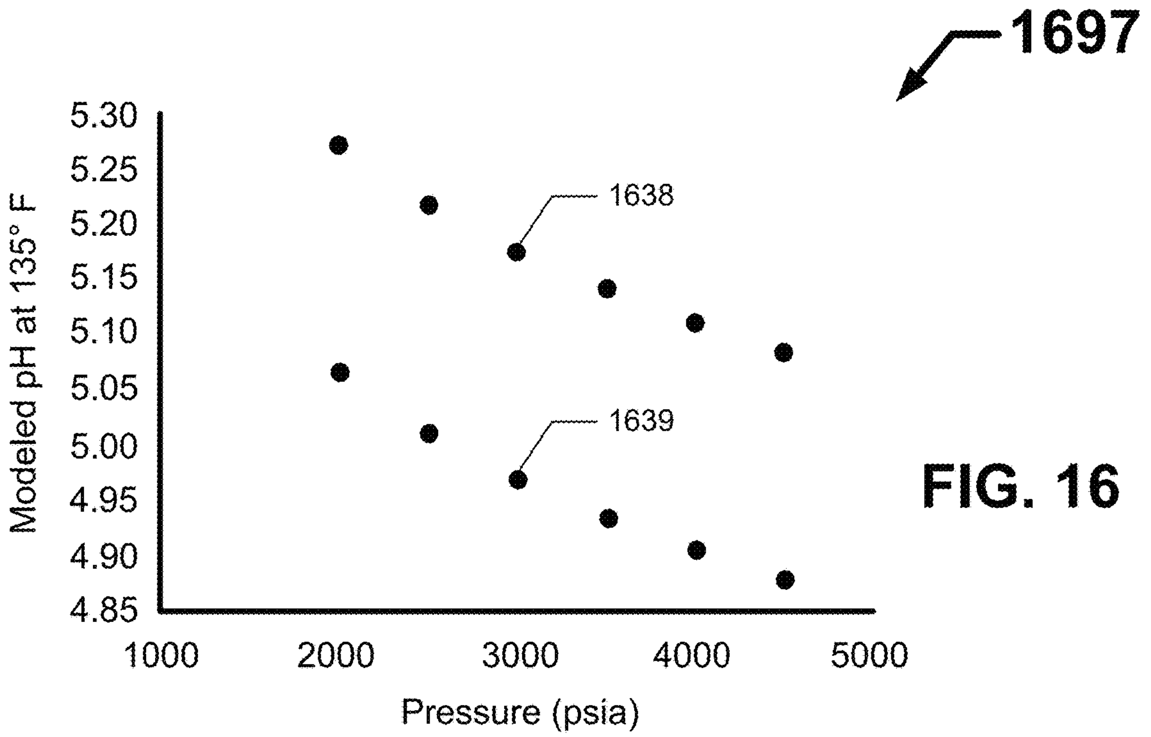

The graph 1697 of FIG. 16 shows plots of modeled in situ pH results under downhole conditions based on different water chemistry inputs. In the graph 1697, the horizontal axis is in terms of potential pressure (in psia) in a wellbore (e.g., wellbore 420), and the vertical axis is in terms of modeled pH of the in situ water at an assumed wellbore pressure. Plot 1638 is a set of 6 data points that show modeled in situ pH at downhole for formation water (e.g., formation water 147) having a certain chemical composition. In this case, the formation water has a pH as high as 5.27 at 2000 psia and as low as 5.08 at 4600 psia. Plot 1639 is a set of 6 data points that show modeled in situ pH at downhole for formation water (e.g., formation water 147) having a different chemical composition relative to the formation water for plot 1638. In this case, the formation water has a pH as high as 5.07 at 2000 psia and as low as 4.88 at 4600 psia. This shows that, using example embodiments, the modeled in situ pH of water may change with the type of water chemistry. The in situ pH modeling results may be utilized as key references to predict water-rock interaction and mange corrosion/scaling risk.

Figure 17:
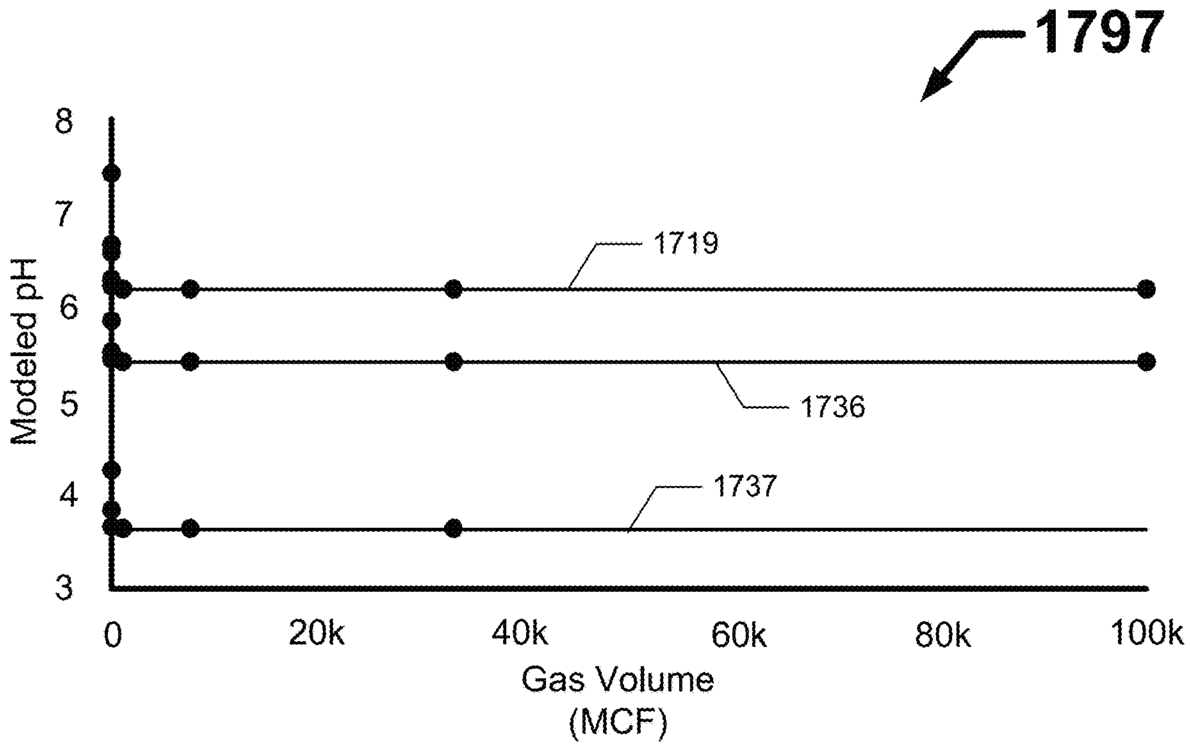

The graph 1797 of FIG. 17 shows plots of modeled in situ pH results under downhole conditions. In the graph 1797, the horizontal axis is in terms of gas volume (in MCF), and the vertical axis is in terms of modeled pH of the in situ water at downhole. All plots in this graph 1797 are for an injection gas with 7.5% $CO_2$, but each plot a different level of alkalinity in the water. Plot 1719 shows modeled pH for a water with an alkalinity level of 6000 ppm. Plot 1736 shows modeled pH for a water with an alkalinity level of 1000 ppm. Plot 1737 shows modeled pH for a water with an alkalinity level of 0 ppm. The modeled results show that the in situ pH under gas injection may be significantly impacted by the alkalinity of the water.

Different from the hydrocarbon gas components, $CO_2$ and $H_2S$ (the acidic gas components) may dissolve and chemically react in the aqueous phase, leading to a change in water chemistry (e.g., in-situ pH) and rock-water interaction (e.g., mineral dissolution/precipitation/transformation) at the subsurface. This $CO_2$/$H_2S$-water-rock interaction may potentially lead to increased porosity and/or permeability of the impacted formation (especially for low permeability shale formations), and consequently increased oil recovery. The chemical reaction with rock itself may positively impact the release of hydrocarbons from rock. At the same time, it may also lead to mineral trapping of $CO_2$ and a change in production risks, including but not limited to scale and/or asphaltene deposition risk at the subsurface.

In some cases, example embodiments may be directed to a method of improving a field operation that comprises a gas injection, where the method may include the step of assessing a plurality of potential injection gases against a plurality of values of a plurality of parameters associated with a plurality of samples, where each of the plurality of potential injection gases comprises an acidic component, and where the plurality of parameters comprises fluid chemistry parameters and rock properties. In such cases, the plurality of parameters may also include at least one of a group consisting of fluid chemistry, minerology, temperature, pressure, and scaling/solid formation potential. In addition, or in the alternative, the plurality of parameters may also include carbon dioxide, hydrogen sulfide content, or both in produced gas.

Further, in such cases, assessing the plurality of potential injection gases against the plurality of values of the plurality of parameters associated with the plurality of samples may include determining target injection pressure. In addition, or in the alternative, assessing the plurality of potential injection gases against the plurality of values of the plurality of parameters associated with the plurality of samples may include determining fluid chemistry of injection water if the field operation comprises the gas injection and the water injection. In addition, or in the alternative, assessing the plurality of potential injection gases against the plurality of values of the plurality of parameters associated with the plurality of samples may include determining gas-water ratio if the field operation comprises the gas injection and the water injection.

In some cases, example embodiments may be directed to a method of improving a field operation that comprises a gas injection, where the method may include the steps of (1) assessing a plurality of potential injection gases against a plurality of values of a plurality of parameters associated with a plurality of samples, where each of the plurality of potential injection gases comprises an acidic component, and where the plurality of parameters comprises fluid chemistry parameters and rock properties, and (2) determining, based on assessing the plurality of potential injection gases against the plurality of values of the plurality of parameters associated with the plurality of samples, a proposed injection gas from among the plurality of potential injection gases for the field operation that comprises the gas injection to be performed using a first wellbore in fluidic communication with a first subterranean formation, a second wellbore in fluidic communication with the first subterranean formation, a third wellbore in fluidic communication with a second subterranean formation, or any combination thereof. In such cases, the method may also include the step of using the proposed injection gas in the field operation comprising the gas injection. In addition, or in the alternative, the method may also include the step of varying at least one of a group consisting of gas-water ratio, fluid chemistry of injection water, and pressure parameters of the field operation comprising the gas injection.

In some cases, example embodiments may be directed to a system for improving a field operation that comprises a gas injection, where the system includes an analysis apparatus. In such cases, the system may also include a sensor device configured to measure the plurality of values of the plurality of parameters associated with the plurality of samples. In addition, or in the alternative, the system may also include a controller communicably coupled to the sensor device and the analysis apparatus, where the controller is configured to control the sensor device and communicate the plurality of values of the plurality of parameters associated with the plurality of samples to the analysis apparatus. In addition, or in the alternative, the system may also include a storage repository communicably coupled to the controller, where the storage repository is configured to store a plurality of algorithms that assess the plurality of potential injection gases against the plurality of values of the plurality of parameters associated with the plurality of samples. In some such cases, the controller may be further configured to modify the plurality of algorithms based on actual results of using the proposed injection gas during the field operation that comprises the gas injection.

In some cases, example embodiments may be directed to a computer-implemented method for improving a field operation comprising a gas injection, where the computer-implemented method may include (1) obtaining a plurality of values of a plurality of parameters associated with a plurality of samples, where the plurality of parameters comprises fluid chemistry parameters and rock properties, (2) facilitate assessing a plurality of potential injection gases against the plurality of values of the plurality of parameters associated with a plurality of samples, where each of the plurality of potential injection gases comprises an acidic component, and (3) facilitate determining, based on facilitating assessment of the plurality of potential injection gases against the plurality of values of the plurality of parameters associated with the plurality of samples, a proposed injection gas from among the plurality of potential injection gases, where the proposed injection gas is used in the field operation comprising the gas injection to be performed using a first wellbore in fluidic communication with a first subterranean formation, a second wellbore in fluidic communication with the first subterranean formation, a third wellbore in fluidic communication with a second subterranean formation, or any combination thereof.

In such cases, the plurality of potential injection gases are assessed simultaneously using a plurality of algorithms. In addition, or in the alternative, facilitating assessment of the plurality of potential injection gases against the plurality of values of the plurality of parameters associated with the plurality of samples comprises determining a pH of in situ water and measuring rock-water interaction using a plurality of algorithms.

Example embodiments may be used to provide systems and methods for evaluating and optimizing (e.g., improving) a field operation comprising a gas injection to improve well performance over multiple stages (e.g., fracturing, shut-in, production). Example embodiments include collecting data associated with rock, water, and hydrocarbons (in gas and/or liquid form) at the subsurface. Example embodiments also test, in a lab and/or using modeling, different injection gases based on the data collected with respect to the subsurface environment. Example embodiments may propose an injection gas (e.g., in terms of composition, in terms of concentration) to use in a field operation on the well at the subsurface. Example embodiments may further monitor the progress of the field operation using the proposed injection gas. Example embodiments may compare actual results with predicted results with respect to the performance of the proposed injection gas, and subsequently make any adjustments (e.g., to the models, to the concentration of the proposed injection gas, to the composition of the proposed injection gas, to the composition of injected water when gas-water alternating injection is utilized, to the composition of injection water when carbonate water injection is utilized) in real time.

Example embodiments may be used to reduce operational risk and impact hydrocarbon product specifications by utilizing components (e.g., $CO_2$, $H_2S$) at the subsurface. Example embodiments may be used to optimize EOR by minimizing scale deposition and/or solid formation at the subsurface. Example embodiments may also extend the useful life of field equipment by minimizing corrosion. Example embodiments may be fully or partially automated. Using example embodiments, tests and evaluations may be conducted in which fluid in the aqueous phase (e.g., carbonated water) is subjected to conditions that are representative of those at the subsurface. Example embodiments may provide a number of benefits. Such benefits may include, but are not limited to, preventing/reducing scale/solid deposition at the subsurface (e.g., in fractures, on frac face, in pore throat), optimizing well performance, enhancing oil recovery, ease of use, extending the life of a well (including both producer and injector), reducing damage (e.g., caused by scale/solid deposition) to field equipment, addressing flow assurance issues, addressing mineral trapping of $CO_2$/appropriate management of unwanted gas, creation of by products that may be used for other purposes, flexibility, configurability, and compliance with applicable industry standards and regulations.

Although embodiments described herein are made with reference to example embodiments, it should be appreciated by those skilled in the art that various modifications are well within the scope of this disclosure. Those skilled in the art will appreciate that the example embodiments described herein are not limited to any specifically discussed application and that the embodiments described herein are illustrative and not restrictive. From the description of the example embodiments, equivalents of the elements shown therein will suggest themselves to those skilled in the art, and ways of constructing other embodiments using the present disclosure will suggest themselves to practitioners of the art. Therefore, the scope of the example embodiments is not limited herein.

What is claimed is:

1. A method of improving a field operation that comprises a gas injection, the method comprising:

assessing a plurality of potential injection gases against a plurality of values of a plurality of parameters associated with a plurality of samples, wherein each of the plurality of potential injection gases comprises an acidic component, and wherein the plurality of parameters comprises fluid chemistry parameters and rock properties, wherein assessing the plurality of potential injection gases against the plurality of values of the plurality of parameters associated with the plurality of samples comprises at least one of a group consisting of determining a pH of in situ water, performing a rock-water interaction study, and determining an impact of the acidic component on scale and asphaltene deposition for a first wellbore in fluidic communication with a first subterranean formation, a surface facility in fluidic communication with the first wellbore, or any combination thereof;

determining, based on assessing the plurality of potential injection gases against the plurality of values of the plurality of parameters associated with the plurality of samples, a proposed injection gas from among the plurality of potential injection gases for the field operation; and providing a chemical composition of a proposed injection gas to generate an injection gas for the gas injection to be performed on the first wellbore in fluidic communication with the first subterranean formation, a second wellbore in fluidic communication with the first subterranean formation, a third wellbore in fluidic communication with a second subterranean formation, or any combination thereof, wherein the injection gas, when used in the gas injection, reduces subsurface scale deposition and/or solid formation to result in at least one of a group consisting of enhanced hydrocarbon recovery, extension of a life of the first wellbore, reduction in damage to field equipment, and optimized performance of the first wellbore.

2. The method of claim 1, wherein assessing the plurality of potential injection gases against the plurality of values of the plurality of parameters associated with the plurality of samples comprises further determining the impact of the acidic component on scale and asphaltene deposition for the second wellbore in fluidic communication with the first subterranean formation, a surface facility in fluidic communication with the second wellbore in fluidic communication with the first subterranean formation, the first subterranean formation, the third wellbore in fluidic communication with the second subterranean formation, a surface facility in fluidic communication with the third wellbore in fluidic communication with the second subterranean formation, the second subterranean formation, or any combination thereof.

3. The method of claim 1, wherein assessing the plurality of potential injection gases against the plurality of values of the plurality of parameters associated with the plurality of samples comprises determining an impact of the acidic component and water chemistry on at least one of a group consisting of hydrocarbon recovery, rock fracture surfaces, and porous media.

4. The method of claim 1, further comprising assessing the proposed injection gas during the field operation comprising the gas injection.

5. The method of claim 4, wherein assessing the proposed injection gas comprises determining an impact of at least one of a group consisting of scale, corrosion, and asphaltene.

6. The method of claim 4, wherein assessing the proposed injection gas comprises monitoring at least one of a group consisting of a production profile, injectivity, and pressure.

7. The method of claim 4, wherein assessing the proposed injection gas comprises evaluating fluid chemistry of produced water, produced gas, and liquid produced hydrocarbons.

8. The method of claim 4, wherein assessing the proposed injection gas comprises evaluating an impact of gas-rock-water interaction and inter-well water migration based on water chemistry data and production data.

9. The method of claim 4, wherein assessing the proposed injection gas comprises assessing mineral trapping of $CO_2$ and mass balance.

10. The method of claim 4, further comprising:

determining that the proposed injection gas, when combined with the plurality of samples in the reaction module, fails to match a forecast, as determined by a model, of how the proposed injection gas reacts with the plurality of samples; and adjusting, using an analysis module, the model based on data collected while the proposed injection gas is combined with the plurality of samples in the reaction module, wherein adjusting the model achieves at least one of a second group consisting of reducing data, improving accuracy, performing efficient correlations, and improved pattern finding.

11. The method of claim 4, further comprising:

determining that actual results differ from expected results predicted when assessing the plurality of potential injection gases against the plurality of values of the parameters associated with the plurality of samples;

assessing the plurality of potential injection gases against the plurality of values of the parameters associated with the plurality of samples using the actual results; and determining, based on assessing the plurality of potential injection gases against the plurality of values of the parameters associated with the plurality of samples using the actual results, a second proposed injection gas from among the plurality of potential injection gases, wherein the second proposed injection gas is used for injection in a subsequent field operation that comprises a gas injection.

12. The method of claim 11, further comprising:

determining for the second proposed injection gas, based on assessing the plurality of potential injection gases against the plurality of values of the parameters associated with the plurality of samples using the actual results, fluid chemistry, and downhole pressure data.

13. The method of claim 1, wherein the field operation comprising the gas injection comprises at least one of a group consisting of gas injection, water alternating gas injection (WAG), and combined and pressurized gas water injection.

14. The method of claim 1, further comprising:

assessing the proposed injection gas when combined with the plurality of samples in a reaction module;

determining that the proposed injection gas, when combined with the plurality of samples in the reaction module, fails to match a forecast, as determined by a model, of how the proposed injection gas reacts with the plurality of samples; and adjusting, using an analysis module, the model based on data collected while the proposed injection gas is combined with the plurality of samples in the reaction module, wherein adjusting the model achieves at least one of a second group consisting of reducing data, improving accuracy, performing efficient correlations, and improved pattern finding.

15. A computer-implemented method for improving a field operation comprising a gas injection, the method comprising:

obtaining a plurality of values of a plurality of parameters associated with a plurality of samples, wherein the plurality of parameters comprises fluid chemistry parameters and rock properties;

facilitate assessing a plurality of potential injection gases against the plurality of values of the plurality of parameters associated with a plurality of samples, wherein each of the plurality of potential injection gases comprises an acidic component, wherein assessing the plurality of potential injection gases against the plurality of values of the plurality of parameters associated with the plurality of samples comprises determining a pH of in situ water and performing a rock-water interaction study, and wherein assessing the plurality of potential injection gases against the plurality of values of the plurality of parameters associated with the plurality of samples further comprises determining an impact of the acidic component on scale and asphaltene deposition for a first wellbore in fluidic communication with a first subterranean formation, a surface facility in fluidic communication with the first wellbore, the first subterranean formation, or any combination thereof;

facilitate determining, based on facilitating assessment of the plurality of potential injection gases against the plurality of values of the plurality of parameters associated with the plurality of samples, a proposed injection gas from among the plurality of potential injection gases; and facilitate providing a chemical composition of the proposed injection gas to generate an injection gas for the gas injection to be performed on the first wellbore in fluidic communication with the first subterranean formation, a second wellbore in fluidic communication with the first subterranean formation, a third wellbore in fluidic communication with a second subterranean formation, or any combination thereof, wherein the injection gas, when used in the gas injection, reduces subsurface scale deposition and/or solid formation to result in at least one of a group consisting of enhanced hydrocarbon recovery, extension of a life of the first wellbore, reduction in damage to field equipment, and optimized performance of the first wellbore.

16. The computer-implemented method of claim 15, further comprising:

obtaining, from a sensor device, a value of a performance parameter of the proposed injection gas during the field operation; and facilitate assessing, using the value of the performance parameter, the proposed injection gas during the field operation comprising the gas injection.

17. The computer-implemented method of claim 15, further comprising:

facilitate adjusting a model used to facilitate assessment of the plurality of potential injection gases against the plurality of values of the plurality of parameters associated with the plurality of samples based on data collected while the proposed injection gas is used during the field operation comprising the gas injection.

18. The computer-implemented method of claim 15, further comprising:

facilitate determining that actual results differ from expected results predicted when facilitating assessment of the plurality of potential injection gases against the plurality of values of the plurality of parameters associated with the plurality of samples;

facilitate assessing the plurality of potential injection gases against the plurality of values of the plurality of parameters associated with the plurality of samples using the actual results; and facilitate determining, based on facilitating assessment of the plurality of potential injection gases against the plurality of values of the plurality of parameters associated with the plurality of samples using the actual results, a second proposed injection gas from among the plurality of potential injection gases, wherein the second proposed injection gas is used in a subsequent field operation comprising a subsequent gas injection.

19. A system for improving a field operation that comprises a gas injection, the system comprising:

an analysis apparatus that is configured to:

assess a plurality of potential injection gases against a plurality of values of a plurality of parameters associated with a plurality of samples, wherein each of the plurality of potential injection gases comprises an acidic component, and wherein the plurality of parameters comprises fluid chemistry parameters and rock properties, wherein assessing the plurality of potential injection gases against the plurality of values of the plurality of parameters associated with the plurality of samples comprises at least one of a group consisting of determining a pH of in situ water, performing a rock-water interaction study, and determining an impact of the acidic component on scale and asphaltene deposition for a first wellbore in fluidic communication with a first subterranean formation, a surface facility in fluidic communication with the first wellbore, or any combination thereof;

determine, based on assessing the plurality of potential injection gases against the plurality of values of the plurality of parameters associated with the plurality of samples, a proposed injection gas from among the plurality of potential injection gases for the field operation; and providing a chemical composition of a proposed injection gas to generate an injection gas for the gas injection to be performed the first wellbore in fluidic communication with the first subterranean formation, a second wellbore in fluidic communication with the first subterranean formation, a third wellbore in fluidic communication with a second subterranean formation, or any combination thereof, wherein the injection gas, when used in the gas injection, reduces subsurface scale deposition and/or solid formation to result in at least one of a group consisting of enhanced hydrocarbon recovery, extension of a life of the first wellbore, reduction in damage to field equipment, and optimized performance of the first wellbore.

* * * * *